(12) United States Patent
Yates et al.

(10) Patent No.: US 11,986,244 B2
(45) Date of Patent: *May 21, 2024

(54) WIDE FIELD FUNDUS CAMERA WITH AUTO-MONTAGE AT A SINGLE ALIGNMENT

(71) Applicant: Retivue, LLC, Charlottesville, VA (US)

(72) Inventors: Paul Andrew Yates, Charlottesville, VA (US); Ming Lai, Charlottesville, VA (US); Ta-Wei Yi, New Taipei (TW); Alex Martinez, Charlottesville, VA (US)

(73) Assignee: RETIVUE LLC, Charlottesville, VA (US)

( * ) Notice: Subject to any disclaimer, the term of this patent is extended or adjusted under 35 U.S.C. 154(b) by 130 days.

This patent is subject to a terminal disclaimer.

(21) Appl. No.: 17/158,632

(22) Filed: Jan. 26, 2021

(65) Prior Publication Data

US 2021/0353144 A1    Nov. 18, 2021

Related U.S. Application Data

(63) Continuation of application No. 16/312,683, filed as application No. PCT/US2017/038560 on Jun. 21, 2017, now Pat. No. 10,925,486.

(Continued)

(51) Int. Cl.
*A61B 3/15*        (2006.01)
*A61B 3/00*        (2006.01)
(Continued)

(52) U.S. Cl.
CPC .............. *A61B 3/158* (2013.01); *A61B 3/00* (2013.01); *A61B 3/0008* (2013.01); *A61B 3/12* (2013.01);
(Continued)

(58) Field of Classification Search
CPC .. A61B 3/158; A61B 3/00; A61B 3/14; A61B 3/0008; A61B 3/152; A61B 3/12;
(Continued)

(56) References Cited

U.S. PATENT DOCUMENTS

| 3,944,342 A | 3/1976 | Martinez |
|---|---|---|
| 4,023,189 A | 5/1977 | Govignon |

(Continued)

FOREIGN PATENT DOCUMENTS

WO    2016040935    3/2016

OTHER PUBLICATIONS

International Search Report and Written Opinion, PCT/ISA/237, International Application No. PCT/US2015/049950, pp. 1-19, International Filing Date Sep. 14, 2015, Search Report dated Jan. 20, 2016.

(Continued)

*Primary Examiner* — Cara E Rakowski
(74) *Attorney, Agent, or Firm* — Simpson & Simpson, PLLC

(57) ABSTRACT

A wide field fundus camera is disclosed to implement multiple illumination beam projectors and to capture multiple retinal images at various viewing angles to facilitate wide field retinal examination. The wide field fundus camera contemplates an ultra-wide field lens that can provide edge to edge imaging of the entire retina at a single alignment. The wide field fundus camera contemplates configuration of said multiple illumination beam projectors to provide visualization of retina and Purkinje reflections simultaneously to facilitate determination of proper camera alignment with the eye. The wide field fundus camera further contemplates control of multiple illumination beam projectors in a programmable manner to further assess alignment of each illumination beam projector with the eye and to capture said (Continued)

multiple retinal images. The wide field fundus camera further contemplates a consumer image recording device with fast auto focusing and fast continuous image capture to make the device easy to use and quick to respond. The wide field fundus camera further contemplates narrow and broad slit beam illuminations to enhance autofocusing, imaging through less transparent crystalline lens, and reduction of haze due to reflected and scattered light from camera and ocular surfaces other than the retina. The wide field camera contemplates a real-time algorithm to reduce said reflected and scattered light haze in said retinal images. The wide field camera further contemplates automated montage of said multiple retinal images into a single wide field FOV retinal montage and automated removal reflected and scattered light haze from said retinal montage. The wide field camera further contemplates to automatically identify camera alignment with the eye and standardize an alignment procedure to simplify reflected and scattered light haze to facilitate dehaze and auto montage of said retinal images.

13 Claims, 29 Drawing Sheets

Related U.S. Application Data

(60) Provisional application No. 62/352,944, filed on Jun. 21, 2016.

(51) Int. Cl.
*A61B 3/12* (2006.01)
*A61B 3/14* (2006.01)
*G06T 5/00* (2006.01)
*G06T 5/50* (2006.01)
*H04N 7/18* (2006.01)

(52) U.S. Cl.
CPC ............... *A61B 3/14* (2013.01); *A61B 3/152* (2013.01); *G06T 5/003* (2013.01); *G06T 5/50* (2013.01); *H04N 7/18* (2013.01); *G06T 2207/20172* (2013.01)

(58) Field of Classification Search
CPC .. G06T 5/003; G06T 5/50; G06T 2207/20172
See application file for complete search history.

(56) References Cited

U.S. PATENT DOCUMENTS

| | | | |
|---|---|---|---|
| 4,247,176 A | 1/1981 | Ito | |
| 5,822,036 A | 10/1998 | Massie et al. | |
| 6,019,472 A | 2/2000 | Koester et al. | |
| 9,288,458 B1 | 3/2016 | Chen et al. | |
| 10,743,764 B2 * | 8/2020 | Yates | A61B 3/125 |
| 10,925,486 B2 * | 2/2021 | Yates | G06T 5/50 |
| 2004/0131249 A1 | 7/2004 | Sandrew | |
| 2004/0156554 A1 | 8/2004 | McIntyre | |
| 2007/0019160 A1 | 1/2007 | Kleen et al. | |
| 2008/0002152 A1 | 1/2008 | Collins et al. | |
| 2008/0259274 A1 | 10/2008 | Chinnock | |
| 2010/0061601 A1 | 3/2010 | Abramoff et al. | |
| 2011/0188775 A1 | 8/2011 | Sun et al. | |
| 2012/0229617 A1 | 9/2012 | Yates et al. | |
| 2012/0287255 A1 | 11/2012 | Ignotovich et al. | |
| 2013/0057828 A1 | 3/2013 | de Smet | |
| 2013/0083184 A1 * | 4/2013 | Yogesan | G02B 19/0028 348/78 |
| 2013/0335704 A1 | 12/2013 | Yates et al. | |

OTHER PUBLICATIONS

Notification of Transmittal, International Search Report, and the Written Opinion of the International Searching Authority dated Oct. 31, 2017 for PCT Application No. PCT/US17/38560; 25 pages.

* cited by examiner

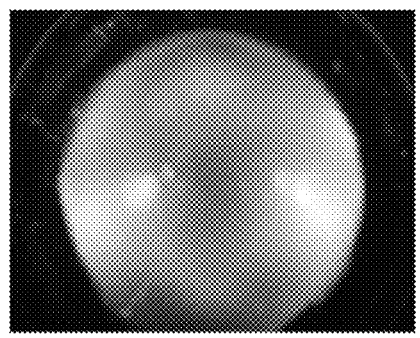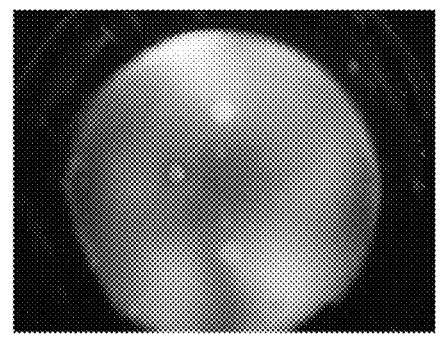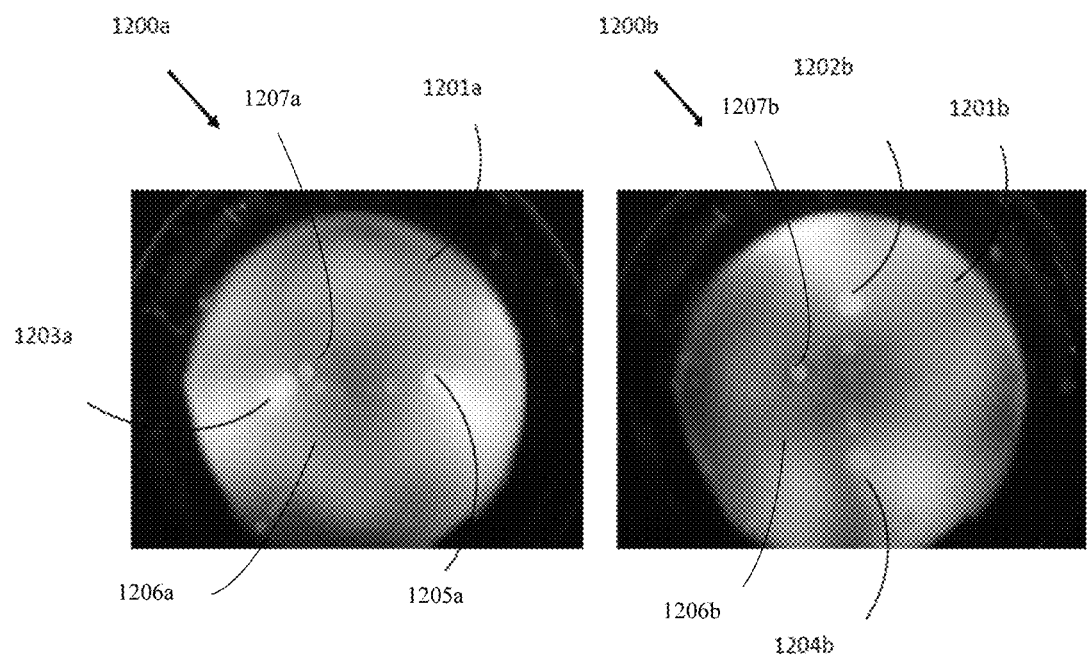
Fig. 12a  Fig. 12b

Gaussian blurred blue channel

Bias

Signal amplifier mask

Characteristic haze pattern with single illuminator

Characteristic haze pattern with single illuminator

Correct alignment 1600a 1601a 1602a

Correct alignment

WIDE FIELD FUNDUS CAMERA WITH AUTO-MONTAGE AT A SINGLE ALIGNMENT

CLAIM OF PRIORITY

This application is a continuation of U.S. Non-Provisional patent application Ser. No. 16/312,683, filed on Dec. 21, 2018, which is a National Stage filing of International Application PCT/US2017/038560 filed on Jun. 21, 2017, which claims benefit of priority of U.S. Provisional Patent Application No. 62/352,944, Yates et al., titled "Wide Field Fundus Camera with Montage at a Single Alignment," filed on Jun. 21, 2016, each of which is hereby incorporated by reference herein in its entirety.

GOVERNMENT RIGHTS

This invention was made with government support under grant number R-44-EY-505 and R44 EY028484 both awarded by National Institute of Heath, National Eye Institute. The government has certain rights in the invention.

TECHNICAL FIELD

The present subject matter relates to a wide field fundus camera for photographing subject retinas.

BACKGROUND

Retinal images are broadly used for diagnosis of various diseases of the human retina. For instance, various retinal cameras have been routinely used to screen and to detect three of the most common eye diseases in adults: diabetic eye disease, glaucoma, and age-related macular degeneration. Early detection of these diseases can delay and prevent subsequent loss of vision. Conventional retina cameras used to perform these screening exams typically have a central 45 to 60-degree field of view (FOV) representing less than 10% of the entire surface area of the retina.

In contrast, wide field retinal images, referring to a greater than 60-degree FOV, are commonly used in the diagnosis of retinopathy of prematurity (ROP), a retinal disease of premature infants. At advanced stages, ROP can result in retinal detachment with permanent vision loss but is often treatable with early routine screening and detection. Traditionally, ROP is typically diagnosed via manual physician exam using an indirect ophthalmoscope. The examining physician utilizes indirect ophthalmoscopy, and relies on scleral depression to visualize the retinal periphery to the or a serrata over eight cardinal positions (12, 1:30, 3:00, 4:30, 6:00, 7:30, 9:00, and 10:30). Given that pathology associated with ROP occurs predominantly in the retinal periphery, a minimum 120-degree FOV of the retina is required for proper diagnosis. Traditional screening and diagnosis of ROP require a highly skilled ophthalmologist to perform this exam and correctly document his/her retinal findings. It is a time-consuming process, and it lacks reliable documentation, with most ophthalmologists still performing sketched drawings to represent their retinal findings.

Wide field retinal images in a digital format can be obtained with the Retcam from Clarity Medical Systems (Pleasanton, California, United States of America). In one approach, a wide field fundus camera employs an illumination ring as shown in U.S. Pat. No. 5,822,036 (Massie et al.) located at the tip of a handpiece housing the illumination light source, imaging optics and camera sensor. The illumination ring is formed with a bundle of optical fibers and projects bright illumination through the entire pupil. The device provides uniform illumination over a field of view to produce a retinal image with a 120-degree FOV of the retina. Use of such a configuration may lack clarity in the image when the crystalline lens is less transparent and when the Purkinje reflection images from the crystalline lens surfaces become visible inside the field of view. Use of such a configuration may be suitable for newborn babies and infants with a highly transparent crystalline lens but may be less suitable for patients with a less transparent lens, in particular, adults.

Furthermore, sufficient retinal examination for ROP detection requires an edge to edge observation of the entire retina, i.e., to cover an 180-degree FOV. The entire retina occupies an ocular hemisphere. An 180-degree FOV refers to a field of view that encompasses this entire ocular hemisphere. A 130 degree FOV device will require a tilt of +/−25 degrees to reach the retinal edge. Imaging of the entire retina with this 130-degree FOV device will necessarily require 6 to 8 separate images with the camera placed at multiple tilt positions relative to the central axis of the eye to image the entire edge of the retina. Sufficient retinal examination with a 130-degree FOV device is time-consuming, and correct tilt alignment of the device with the eye for edge to edge imaging of the retinal periphery to detect ROP remains difficult, even for a well-trained ophthalmologist.

SUMMARY

Newborn babies and infants may have a less-transparent crystalline lens, due to various clinical conditions. Image haze may appear due to light scattering inside the cornea or less-transparent crystalline lens wherever the illumination beam path overlaps with imaging beam path. This image haze may also stem from Purkinje reflection images from corneal (i.e. Purkinje I and II) and crystalline lens surfaces (i.e., Purkinje III and IV). We refer to image haze as scattered or reflected light off any ocular or camera surface, other than the retina, wherein this scattered or reflected light can reach the recording sensor of a retinal camera.

Image haze may be improved by optical techniques separating the illumination beam path from the image beam path inside the crystalline lens. This configuration can be found in conventional retinal cameras, but with a limit on the field of view of 45 to 60 degrees and with various masks on the illumination beam path to create an image window throughout the crystalline lens. However, such a configuration remains a challenge to implement for a wider field of view fundus camera.

Another highly desirable feature for fundus cameras would be a quick and reliable autofocus. Unlike conventional tabletop fundus cameras, a wide field fundus camera for ROP screening is typically a handheld device, and thus fast response of the camera may improve the usability of the device. Generally, autofocus found in conventional tabletop fundus cameras is much slower than found in consumer image recording devices. There have been prior attempts to implement a consumer image recording device with fast autofocus into a handheld fundus camera.

In US patent application publication US 2012/0229617, titled "Hand-Held Portable Fundus Camera for Screening Photography," Yates et al. disclose how to implement a consumer image recording device into a handheld fundus camera to utilize autofocus mechanisms built into a consumer camera. Another concern is the reliability as autofocus in consumer image recording devices may rely on well-illuminated, and high contrast features to perform, while retinal images may lack such well-illuminated and high contrast features. In US patent application publication US 2013/0335704, titled "Intuitive Techniques and Apparatus for Ophthalmic Imaging," Yates et al. disclose how to project a diffractively-modified laser beam to create well-illuminated and high contrast features on the retina to enhance auto focusing. A further challenge arises as to how to implement the concept with non-coherent light and how to improve performance through less-transparent crystalline lenses.

Auto focusing and imaging through a less-transparent crystalline lens remains a challenging issue for wide field fundus cameras with a wide field of view. Instrumenting an indirect ophthalmoscope into a digital format and adapting a consumer image recording device and its fast autofocus have yet to be implemented for wide field fundus cameras.

An example according to the present subject matter contemplates a wide field fundus camera to implement multiple illumination beam projectors, of which each illumination beam projector mimics the illumination conditions of an indirect ophthalmoscope. An example according to the present subject matter thus contemplates taking multiple retinal images at various viewing angles to mimic viewing conditions of the indirect ophthalmoscope. An example according to the present subject matter also contemplates implementing a wide field fundus camera with an image recording device that enables autofocus, auto exposure, real-time display and wireless transfer of high definition images. An example according to the present subject matter further contemplates projecting a narrow slit beam at an angle to enhance autofocus through a less-transparent crystalline lens. An example according to the present subject matter also further contemplates implementing a broad slit beam into each of multiple illumination beam projectors to better image through a less-transparent crystalline lens. An example according to the present subject matter contemplates positioning of said multiple illumination beam projectors in axially symmetric positions around a central viewing axis. A further example according to the present subject matter contemplates coupling said multiple illumination beam projectors to a central viewing axis using a beam splitter or mirror. An example according to the present subject matter further contemplates implementing an illumination beam projector that can simultaneously illuminate the retina and provide Purkinje reflections within the wide-field FOV to facilitate simultaneous visualization of the retina and Purkinje reflections to determine camera alignment with the eye. A further example according to the present subject matter contemplates multiple axially symmetric illumination beam projectors to illuminate the retina and provide Purkinje reflection within the wide-field FOV to facilitate axial centration of the camera with the eye. An example according to the present subject matter further contemplates implementing image processing to stitch multiple retinal images into an evenly exposed single field image.

To achieve edge to edge observation of the entire retina at a single alignment, an ultra-wide FOV lens of 180 degrees is highly desirable. An example according to the present subject matter contemplates implementing a contact lens system (i.e., a lens having a surface to contact an eye) with a 160-degree FOV or wider. The contact lens system comprises one or more aspherical surfaces. The term "ultra-wide FOV" refers to 160 degrees FOV or wider.

For ultra-wide FOV imaging, reflections (i.e., Purkinje I and II) and scattering haze from the cornea become unavoidable. An example according to the present subject matter contemplates placing all the Purkinje reflections into clusters of scattering haze and to allow removal of said Purkinje reflections and scattering haze with digital masks. A further example according to the present subject matter contemplates placing Purkinje reflections into clusters of scattering haze by one or more of the following: adjustment of the angle of the illumination projector beam with the visual axis, adjustment of illumination projector beam shape, or adjustment of illumination projector beam spot size). A further example according to the present subject matter contemplates placing Purkinje reflections into clusters of scattering haze by one or more of the following: adjustment of said wide-angle or ultra-wide angle FOV lens aspherical surface curvature or lens aperture.

Image haze in retinal images differs fundamentally from diffuse atmospheric haze in outdoor photos. Retinal image haze is directional, produced by scattering of the incident illumination used to examine the eye, has different scattering characteristics depending on which ocular surface is being illuminated by this light (cornea, lens, iris), has different polarization characteristics, has different spatial characteristics depending on the position of the scattering surface, and has different spectral characteristics from atmospheric haze. While the general problem of removing atmospheric haze from photographic images has been previously considered (eg U.S. Ser. No. 12/697,575), these models assume an orthogonal relationship between the illuminating source (eg. the Sun) creating the scattering light as compared to the camera photographing the image and the object being photographed. Mathematical models of such haze conditions generate unique solutions for removing haze from outdoor images that are not optimized for reduction or elimination of retinal image haze. Estimating a haze map for retinal images requires consideration of the characteristics of the illumination source and the scattering surfaces of the eye which generate this image haze.

A further example according to the present subject matter contemplates digital removal of reflection and scattering haze through identification of characteristics of the reflection and scattering haze component to differentiate it from the retinal image of the image. An example according to the present subject matter contemplates determination of the reflection and scattering haze component of the sectional image, as opposed to the retinal component, using one or more differentiating features that include spectral, positional, shape, size, sharpness, uniformity, detail, directional, and distribution pattern of said reflection and scattering haze created by said illumination beam projectors. A further example contemplates optical modeling of expected haze pattern from a directed light source as provided by said illumination beam projector to further assist in identification of reflection and scattering haze. A further example contemplates automated identification of Purkinje reflections in captured retinal images to assess camera alignment with an eye to allow prediction of expected reflection and scattering haze to further facilitate removal of reflection and scattering haze.

Removal of reflection and scattering haze can facilitate photographer visualization of retinal detail to determine the presence of retinal pathology, determination of camera centration and tilt with respect to the central visual axis of the eye, and determination of retinal focus by the camera prior to capture of a retinal image. In PCT/US2015/049950, Yates et al contemplated removal of reflection and scattering haze following acquisition of sequential images. An example according to the present subject matter contemplates real-time removal of reflection and scattering haze to permit retinal camera positioning and retinal image composition prior to retinal image capture. We refer to real-time as removal of reflected and scattering haze in less than 200 milliseconds to allow display of de-hazed retinal images on an image display at a rate greater than five frames per second. An example according to the present subject matter contemplates display of de-hazed retinal images on an image display at a frame rate greater than or equal to 30 frames per second during alignment of the wide-field camera with the eye, prior to sectional retinal image capture.

Removal of scattering haze can facilitate visualization of Purkinje reflections. Purkinje reflections can be used to determine the alignment of the camera with respect to the central axis of the eye. An example according to the present subject matter contemplates removal of reflection and scattering haze, except for discrete Purkinje reflections, to maximize visualization of said discrete Purkinje reflections to improve assessment of camera alignment with the eye.

Removal of reflection and scattering haze on captured retinal images can facilitate the creation of a wide-field full FOV image with enhanced image clarity to allow examination of retinal pathology. An example according to the present subject matter contemplates reflection and scattering haze removal on sectional retinal images following retinal image capture. An example according to the present subject matter contemplates use of digital masks to remove sections of the sectional images with prominent purkinje reflections and scattered haze. A further example according to the present subject matter contemplates dehazing of the sectional image by estimating and refining a transmission map based on known characteristics of the reflected and scattered haze and a reference retinal transmission map. A further example according to the present subject matter contemplates dehazing of the sectional image by determining camera alignment with the central axis of the eye using the pattern of Purkinje reflections. Once camera alignment is determined, an estimated haze map is computed using a reference haze model for corneal, iris, and lens reflection and scattered haze for this particular alignment. Sectional images with the reflection and scattering haze removed can then be assembled into a single image of full FOV. A further example according to the present subject matter contemplates removal of residual reflection and scattering haze removal on the assembled full FOV single image.

In general a montage image is constructed from individual component images to create a wider panorama. This problem has been previously considered for retinal images. However, proposed algorithms must necessarily consider rotational, translational, tilt, and magnification differences inherent in individually acquired retinal images. General panorama stitching algorithms are ill suited to the task given there are few high contrast retinal features to easily enable determination of overlap between images and automatic control point generation used in montage algorithms. This requires any number of techniques including skeletonization of the retinal vasculature or searching for optimal spectral frequency overlap between images. There is further a need to determine which portion of two or more retinal images that overlap to display. Finally, there is the general need to blend overlapped images to create a seamless border and create the impression of a single seamless panoramic image. The complexity of this problem frequently results in misalignments between component images in the computed montage, visible seams between images with a "collage-like" appearance to the final image, large contrast variation throughout the image, and very slow processing speed given the number of parameters that must be optimized when few assumptions can be made about the characteristics of and relationships between each image. A single montage of 10 images may take 30 minutes to several hours to generate.

An example according to the present subject matter contemplates to assemble sectional images into a single montage automatically and instantly. We refer to automatically as not requiring user intervention to generate the full FOV montage from the sectional images. An example according to the present subject matter contemplates generation of a full FOV montage in less than 5 seconds to allow user review of the captured wide-field retinal image to quickly determine the presence of retinal pathology and the need to capture additional retinal images. An example according to the present subject matter contemplates a montage algorithm that uses one or more simplifying assumptions about the structure of the sectional images to rapidly generate a single, seamless, well exposed, full FOV montage. These simplifying assumptions include one or more of stereotypical spatial position, image exposure, focus, tilt, specular reflections, illumination pattern, and haze patterns for these sectional images. These simplifying assumptions allow one or more of automatic determination of sectional image overlap, automatic generation of control points for computing a montage, automatic determination of which sectional image to display in overlapping areas based on characteristic exposures in each sectional image, ability to automatically digitally mask off Purkinje reflections and scattering haze based on characteristic haze patterns, generation of a seamless blend at sectional image overlaps, adjustment of exposure throughout the montage based on understanding the structure and position of the illumination beam projector used to take each sectional image with respect to the central axis of the eye. An example according to the present subject matter contemplates that sectional images are taken with a plurality of illumination beam projectors at high-speed so as to minimize eye movement between each sectional image. If the eye does not move between each sectional image then it can be assumed that all sectional images are automatically aligned with one another without needing to shift the position of each sectional image when generating a full wide field FOV montage image.

The present invention contemplates the use of an ultra-wide field lens to cover 180-degree FOV. The present invention also contemplates obtaining centered and on-axis alignment to standardize the haze spot locations and to stereotype the reflection and scattering haze pattern. The present invention further contemplates real-time dehazing of retinal images to enable better judgment of proper alignment of the wide-field camera with the eye and proper retinal focus. The present invention further contemplates capture of multiple sectional images of the desired FOV quickly at a single alignment. The present invention further contemplates capture of multiple sectional images to cover an 180-degree FOV at a single alignment. The present invention further contemplates dehazing of sectional retinal images to enhance visualization of retinal detail. The present invention still further contemplates employing an auto-montage algorithm to perform automatic stitching of the sequential images into a single montage of the full retinal FOV defined with the ultra-wide field lens.

In PCT/US2015/049950, Yates et al contemplated a montage algorithm where assumed symmetry of retinal illumination and haze in individual sectional images, due to central alignment of the wide field fundus camera with the central axis of the eye, allowed for simplified construction of the montage image. A further example according to the present subject matter contemplates to automatically alter assumed symmetries and the relationship between sectional images using the computed alignment of the wide field fundus camera with respect to the eye. In this manner, the automated montage algorithm can automatically and quickly adjust for any central misalignment between eye and wide field fundus camera which might create asymmetries in reflected and scattered haze as well as retinal illumination patterns in sectional images. This adjustment would allow for automated and instant montage generation to generate a full single wide field FOV even for sectional images where the wide field fundus camera is in a non central alignment with respect to the eye. In a further example according to the present subject matter, assymetric areas from each sectional image may be used to generate the wide field FOV montage. In another example according to the present subject matter, asymmetric digital masks may be generated to mask asymmetric haze in said sectional images to produce said asymmetric areas from each sectional image used to generate the wide field FOV montage.

Consequently, the present invention contemplates to achieve an auto-montage of sufficient FOV from sequential sectional images taken at any single alignment of the wide field fundus camera with the eye, to improve usability and improve visualization of retinal details to enable tele-screening of ROP and other retinopathies.

More specifically, an example according to the present subject matter discloses a wide field fundus camera, comprising:

an aspherical lens having a symmetric viewing axis and disposed to form a retinal image, wherein said aspherical lens is an element of a wide-field or an ultra-wide field objective lens;

an image recording device configured to provide one or more of auto focus and auto exposure and aligned with said aspherical lens to capture said retinal image;

a first source configured to provide a plurality of illumination beam projectors positioned around said viewing axis and projected each at an angle toward said aspherical lens, wherein two or more illumination beams are arranged in an axial symmetric configuration relative to the viewing axis to provide centered and on-axis alignment guidance;

a second source configured to provide a narrow illumination beam projector projected at an angle and away from pupil center to provide a bright feature on the retina to enhance autofocusing through less-transparent crystalline lens;

cross polarization optics incorporated between said first and second sources of illumination beams and said image recording device to reject specular reflections of said illumination beams and reduce reflected and scattered light haze;

a real-time dehazing algorithm implemented to remove reflected and scattered light from the retina image to facilitate improved judgment of proper camera alignment with the eye and retinal image focus;

an electronic control circuit configured to provide a system to control said plurality of illumination beam projectors and facilitating capture of a plurality of retinal images in a programmable manner; and an automatic montage algorithm configured to process said captured plurality of retinal images to mask out hazed areas, remove reflected and scattered haze, and to stitch the captured plurality of images into a wide-field or ultra-wide field composite image.

Therefore, a first aspect of the present subject matter can include providing a wide field fundus camera implementing multiple illumination beam projectors and multiple retinal images at various viewing angles to mimic retinal examination with an indirect ophthalmoscope. A second aspect of the present subject matter can include the use of a consumer image recording device having fast auto focusing so as to make a wide field fundus imaging apparatus quick to respond and easy to use. A third aspect of the present subject matter can include the use of a consumer image recording device having high-speed continuous image capture (greater than five captured images per second) so as to facilitate capture of multiple sectional images from said multiple illumination beam projectors to provide a full FOV prior to movement of the eye. A fourth aspect of the present subject matter can include providing narrow and broad slit beam illuminations to enhance autofocusing and imaging through less transparent crystalline lens and reflection haze. A fifth aspect of the present subject matter can include the use of an ultra-wide field lens to enable edge to edge detection of the entire retina. A sixth aspect of the present subject matter can include the use of the multiple illumination beams to form guidance for central and on-axis alignment. A sixth aspect of the present subject matter can include the use of real-time dehazing to form guidance for central and on-axis alignment. A seventh aspect of the present subject matter can include the use of real-time dehazing and automatic montage of captured sectional retinal images to form a full FOV wide-field or ultra-widefield retinal image.

A first aspect of the invention is directed to a wide field fundus camera comprising an objective lens having a viewing axis and disposed to form a retinal image, an image recording device disposed to capture said retinal image of said wide field of view, a plurality of illumination beam projectors positioned around said viewing axis and each configured to project an illumination beam at an angle toward said objective lens, a mechanism of cross polarization configured between said image recording device and said plurality of illumination beam projectors to reject specular reflections of said illumination beams, an image display operatively coupled to the image recording device to display said retinal image from said image recording device, an electronic controller operatively coupled to said plurality of illumination beam projectors to provide power to each of the plurality of illumination beam projectors in a predetermined sequence to provide illumination to obtain each of a plurality of retinal images, and at least one computing processor programmed to execute a real-time dehazing algorithm to perform real-time removal of reflection and scattered light haze, and at least one computing processor programmed to execute an automated montage algorithm to produce an automated montage of said plurality of retinal images into a single image of said wide field of view.

The camera may further comprise a computing processor programmed to execute a dehazing algorithm to further remove reflected and scattered light haze from said montage image.

In some embodiments, the objective lens is a wide field aspherical lens having a FOV of 60 degrees to 160 degrees. The objective lens may be an ultra-wide field objective lens having a FOV of 160 degrees or wider. The objective lens may be an ultra-wide field objective lens system comprising a contact lens, a meniscus lens and an aspherical lens.

In some embodiments, the plurality of illumination beam projectors are optically coupled to a plurality of mirrors or beamsplitters to direct light from said projectors along the viewing axis.

In some embodiments, the image recording device is a camera configured to provide automatic focusing, automatic exposure selection, and continuous image capture.

In some embodiments, the real-time dehazing algorithm identifies reflected and scattered light haze in said retinal images by position of said haze.

In some embodiments, real-time dehazing algorithm identifies reflected and scattered light haze in said retinal images by spectral content of said haze. The real-time dehazing algorithm may identify camera alignment with the eye and determines expected reflected and scattering haze patterns for this camera alignment to facilitate identification and removal of said reflected and scattering haze.

In some embodiments, the automated montage algorithm identifies camera alignment with the eye and combines said plurality of said retinal images camera into a single full FOV montage for said camera alignment.

In some embodiments, the plurality of illumination beam projectors comprises 4 projectors positioned to provide four reflection spots at 12, 3, 6, and 9 o'clock positions on an eye positioned along the viewing axis.

In some embodiments, two of said illumination beams are located at the 12 and 6 o'clock positions along the viewing axis and two of said illumination beams are located at the 3 and 9 o'clock positions along the viewing axis. In some embodiments, the plurality of illumination beam projectors comprises of 8 projectors positioned to provide eight reflection spot clusters at 12, 1:30, 3, 4:30, 6, 7:30, 9, and 10:30 o'clock positions on an eye positioned along the viewing axis.

In some embodiments, 4 of the 8 projectors form a first subset providing infrared illumination and 4 of the 8 projectors form a second subset providing white light illumination, each of the first subset and the second subset being symmetrically disposed around viewing axis.

The mechanism of cross polarization may be aligned with a polarization axis of the eye to reduce reflected and scattered light haze from the eye.

In some embodiments, the illumination beam projectors are configured to provide simultaneous retinal illumination and visible ocular Purkinje reflections to assess camera alignment with the retina.

In some embodiments, the real-time dehazing algorithm comprises processor accessible instructions for dehazing an image from a wide field fundus camera, that when executed perform acts comprising computing position of purkinje reflections from said wide field fundus camera produced by said illumination beam projectors, computing wide field fundus camera alignment with central axis of eye being imaged by said wide field fundus camera using position of said purkinje reflections within said image from said wide field fundus camera, computing an estimated haze map for said wide field fundus image using reference ocular corneal and lens reflected and scattering haze model for said illumination beam projector at said camera alignment with said central axis of a reference model eye, computing a digital mask for removal of reflected and scattering haze from said wide field fundus image using estimated haze map, computing a processed masked wide field fundus image from said wide field fundus image by removal of portions of said wide field fundus image covered by said digital mask, computing a transmission map utilizing estimated haze map for said wide field fundus image, refining a transmission map for said wide field fundus image using reference retinal wide field fundus image, recovering a retinal image from said masked wide field fundus image using the refined transmission map to dehaze the masked wide field fundus image and produce a dehazed masked wide field retinal image.

In some embodiments, the real-time dehazing algorithm comprises processor-accessible instructions for dehazing an image from a wide field fundus camera, that when executed perform acts comprising computing an estimated haze map using at least one of a reference spectrum and size and spatial distribution of said reflected and scattering haze, computing a transmission map utilizing estimated haze map for said wide field fundus image, refining a transmission map utilizing estimated retinal transmission from reference retinal wide field fundus image, recovering a retinal image from said wide field fundus image using the computed transmission map to dehaze the wide field fundus image and produce a dehazed wide field retinal image.

In some embodiments, the automated montage algorithm comprises processor accessible instructions for montaging sectional images from a wide field fundus camera into a single FOV wide field fundus image, that, when executed, performs acts comprising computing position of purkinje reflections from said wide field fundus camera produced by said illumination beam projectors, computing wide field fundus camera alignment with central axis of eye being imaged by said wide field fundus camera using position of said purkinje reflections within said sectional images from said wide field fundus camera, computing an area of each said sectional image to be included in said montage image and creating a sectional image digital mask for each said sectional image to remove scattering haze and Purkinje reflections, determined by said wide field fundus camera alignment, computing a masked sectional image from said wide field fundus camera sectional image by removal of the area of each said sectional image covered by each said sectional image digital mask, computing a blending of overlapping areas of each said sectional image using one or more of sectional image exposure, wide field fundus camera alignment, sectional image haze, sectional image focus, sectional image spatial frequencies, and sectional image sharpness to preserve said montage image fine structural detail while evening out said montage image exposure to create a seamless montage, computing an image projection for said montage image by using said wide field fundus camera alignment to minimize montage image distortion.

Another aspect of the invention is directed to a wide field fundus camera comprising an objective lens having a viewing axis and disposed to form a retinal image, an image recording device disposed to capture said retinal image of said wide field of view, a plurality of eight illumination beam projectors positioned symmetrically around said viewing axis and each configured to project an illumination beam at an angle toward said objective lens, a mechanism of cross polarization configured between said image recording device and said plurality of illumination beam projectors to reject specular reflections of said illumination beams, an image display operatively coupled to the image recording device to display said retinal image from said image recording device, an electronic controller operatively coupled to said plurality of eight illumination beam projectors to provide power to each of the plurality of illumination beam projectors in a predetermined sequence to illuminate for each sequential image two of said illumination beam projectors with said illumination beam projectors positioned 180-degrees from one another around said viewing axis, and at least one computing processor programmed to execute a real-time dehazing algorithm to perform real-time removal of reflection and scattered light haze; at least one computing processor programmed to execute an automated montage algorithm to produce an automated montage of said two or four sequential retinal images into a single image of said wide field of view, and at least one computing processor programmed to execute a dehazing algorithm to further remove residual reflection and scattered light haze from said automated montage image to create a haze free montage image In some embodiments, the camera is configure to acquire two sequential images using said electronic controller powering two said illumination beam projectors positioned in a symmetric matter about the viewing axis with illumination beam projectors at 12 o'clock and 6 o'clock powered for the first sequential image and 3 o'clock and 9 o'clock powered for the second sequential image. In some embodiments, the two sequential images are acquired using said electronic controller powering two said illumination beam projectors positioned in a symmetric matter about the viewing axis with illumination beam projectors at 10:30 o'clock and 4:30 o'clock powered for the first sequential image and 1:30 o'clock and 7:30 o'clock powered for the second sequential image. In some embodiments, four sequential images are acquired using said electronic controller powering two said illumination beam projectors positioned in a symmetric matter about the viewing axis with illumination beam projectors at 12 o'clock and 6 o'clock powered for the first sequential image, 3 o'clock and 9 o'clock powered for the second sequential image, 10:30 o'clock and 4:30 o'clock powered for the third sequential image and 1:30 o'clock and 7:30 o'clock powered for the fourth sequential image.

The objective lens may be a wide field aspherical lens having a FOV of 60 degrees to 160 degrees. In some embodiments, the objective lens is an ultra-wide field objective lens having a FOV of 160 degrees or wider.

In some embodiments, the objective lens is an ultra-wide field objective lens system comprising a contact lens, a meniscus lens and an aspherical lens.

Still another aspect of the invention is directed to a method of operating a wide field fundus camera, comprising the steps of providing an objective lens having a viewing axis and disposed to image a retina having a fundus, the viewing axis being in first alignment with the retina, providing an image recording device disposed to capture said retinal image; providing a plurality of illumination beam projectors positioned around said viewing axis and projected each at a predetermined angle with respect to said viewing axis, providing a mechanism of cross polarization configured between said image recording device and said plurality of illumination beam projectors to reject specular reflections of said illumination beams; providing an image display configured to display said retinal image from said image recording device, providing a computing processor coupled with said image recording device and said image display to enable real-time image processing and display, providing a real-time dehazing algorithm incorporated in said computing processor to perform real-time removal of reflection and scattered light haze, providing an electronic controller powering said plurality of illumination beam projectors in a programmable manner, capturing a plurality of fundus images at the first alignment, each image captured with the plurality of illumination beam projectors in a corresponding state of illumination, at least two of the states of illumination being different than one another, and providing an automated montage algorithm incorporated in said computing processor to perform automated montage of said plurality of retinal images into a single montage image of said wide field of view.

In some instances the plurality of fundus images comprises two images, each of the two images generated using illumination from only a corresponding two, axial-symmetrically disposed illumination beam projectors of the plurality of illumination beam projectors.

In some instances the plurality of fundus images comprises four images, each of the four images generated using illumination from only a corresponding two, axial-symmetrically disposed illumination beam projectors of the plurality of illumination beam projectors.

In some instances, the plurality of fundus images comprises four images, each of the four images generated using illumination from a corresponding one of the plurality of illumination beam projectors.

In some instances, the plurality of fundus images may comprise eight images, each of the eight images generated using illumination from a corresponding one of the plurality of illumination beam projectors.

The method may further comprise a dehazing algorithm incorporated in said computing processor to further remove reflected and scattered light haze from said montage image.

Yet another aspect of the invention is directed to a computer-readable storage medium including instructions for a dehaze algorithm for a wide field fundus camera comprising processor accessible instructions for dehazing an image from a wide field fundus camera, that when executed perform acts comprising computing position of purkinje reflections from said wide field fundus camera produced by said illumination beam projectors, computing wide field fundus camera alignment with central axis of eye being imaged by said wide field fundus camera using position of said purkinje reflections within said image from said wide field fundus camera, computing an estimated haze map for said wide field fundus image using reference ocular corneal and lens reflected and scattering haze model for said illumination beam projector at said camera alignment with said central axis of a reference model eye, computing digital mask for removal of reflected and scattering haze from said wide field fundus image using estimated haze map, computing processed masked wide field fundus image from said wide field fundus image by removal of portions of said wide field fundus image covered by said digital mask, computing transmission map utilizing estimated haze map for said wide field fundus image, refining transmission map for said wide field fundus image using reference retinal wide field fundus image, and recovering retinal image from said masked wide field fundus image using the refined transmission map to dehaze the masked wide field fundus image and produce a dehazed masked wide field retinal image.

Still another aspect of the invention is directed to a computer-readable storage medium including instructions for a dehaze algorithm for a wide field fundus camera comprising processor accessible instructions for dehazing an image from a wide field fundus camera, that when executed perform acts comprising computing estimated haze map using at least one of reference spectrum and size and spatial distribution of said reflected and scattering haze computing transmission map utilizing estimated haze map for said wide field fundus image, refining transmission map utilizing estimated retinal transmission from reference retinal wide field fundus image, and recovering retinal image from said wide field fundus image using the computed transmission map to dehaze the wide field fundus image and produce a dehazed wide field retinal image.

Yet another aspect of the invention is directed to a computer-readable storage medium including instructions for an automated montage algorithm for a wide field fundus camera comprising processor accessible instructions for montaging sectional images from a wide field fundus camera into a single FOV wide field fundus image, that when executed perform acts comprising computing position of purkinje reflections from said wide field fundus camera produced by said illumination beam projectors, computing wide field fundus camera alignment with central axis of eye being imaged by said wide field fundus camera using position of said purkinje reflections within said sectional images from said wide field fundus camera, computing the area of each said sectional image to be included in said montage image and creating a sectional image digital mask for each said sectional image to remove scattering haze and Purkinje reflections, determined by said wide field fundus camera alignment, computing masked sectional image from said wide field fundus camera sectional image by removal of area of each said sectional image covered by each said sectional image digital mask, computing stitching of said masked sectional images into a single, and computing blending of overlapping areas of each said sectional image using one or more of sectional image exposure, wide field fundus camera alignment, sectional image haze, sectional image focus, sectional image spatial frequencies, and sectional image sharpness to preserve said montage image fine structural detail while evening out said montage image exposure to create a seamless montage, computing an image projection for said montage image by using said wide field fundus camera alignment to minimize montage image distortion, and computing said single FOV wide field fundus image.

These and other aspects of the invention will become more apparent in the following drawings, detailed description, and claims.

BRIEF DESCRIPTION OF THE DRAWINGS

FIG. 11 shows an illustrative example of a photo image of one embodiment of an ultra-wide field fundus camera used to capture an ultra-wide field FOV of a baby retina. Four illumination beam projectors are turned on positioned at 12, 3, 6, and 9 o'clock around said viewing axis. Purkinje reflections and scattering haze are evident.

FIG. 12 shows an illustrative example of two sequential photo images taken of a baby retina with an ultra-wide field fundus camera with FIG. 12a having illumination beams positioned at 3 and 9 o'clock relative to the viewing axis turned on. In FIG. 12b illumination beams positioned and 12 and 6 o'clock relative to the viewing axis are turned on. Purkinje reflections and reflected and scattering light haze are evident in both FIG. 12a and FIG. 12b, with different haze patterns based on camera alignment with the eye and which illumination beam projectors are turned on.

FIG. 13 shows an illustrative example of an automated montage generated from sequential photo images take of a baby retina with an ultra-wide field fundus camera. In FIG. 13a Purkinje reflections as well as reflected and scattering haze have been partially removed to generate a single FOV montage that has enhanced visualization of retinal detail as compared to FIG. 12a or FIG. 12b.

FIG. 14b shows an illustrative example of a blue channel isolated from a retinal image. It was generated from FIG. 14a.

FIG. 16b shows an illustrative example of a retinal image taken with incorrect camera alignment, demonstrated via skewed P4 Purkinje reflections and illuminated by 4 beam illuminators. It was taken from the same eye as FIG. 16a.

DETAILED DESCRIPTION

Figure 1:
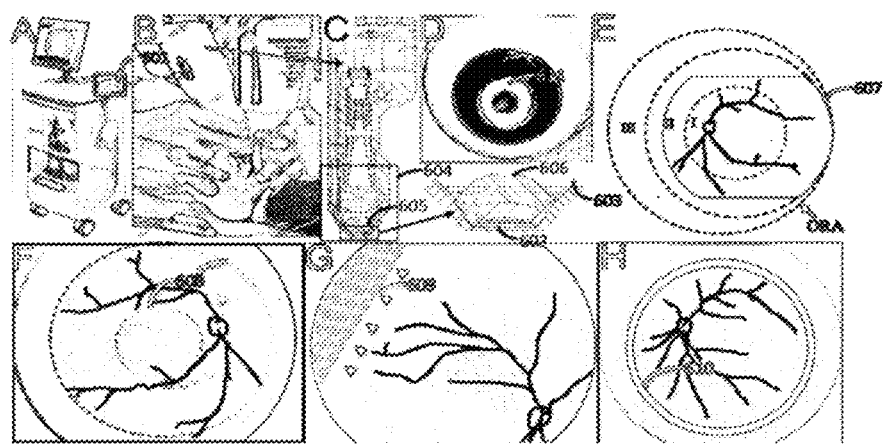
FIG. 1. illustrates a generally-available camera and related techniques for ROP screening.

FIG. 1 shows the Retcam contained on a rolling cart with a handheld imaging camera 601. A computer on the cart connects to the camera sensor inside the handheld imaging camera. Halogen illumination on the cart connects via fiber optic cable to the handpiece. B The contact lens 602 of the handpiece is positioned on the neonate's cornea following dilation and lid speculum placement C, D Fiber optic illumination 603 is routed thru the lens module 604 to the front of the handpiece 605 at the sides of the imaging lens 606 to create ring illumination 611. E Representative field of the entire retina divided into zones I, II, and III used for retinopathy of prematurity screening (ROP). Direct ring illumination may cover a 120-degree field of view allowing macular centered pictures to reach zone II of the retina, but requiring repositioning of the handpiece in up to 9 locations to fully image the entire peripheral retina in zone III to the Ora Serrata 607. F Ring illumination may create a "donut" in some patients 608, with illumination falling off peripherally and centrally. G Some peripheral details of the retina such as a demarcation line associated with ROP (609—white arrows) may be less visible if there is insufficient peripheral illumination of the retina. H In adult patients there may be prominence of the human lens reflection (Purkinje III and IV reflection) of the ring illumination, which occurs due to changes in the refractive power of the human lens following the neonatal period 610.

Figure 2:
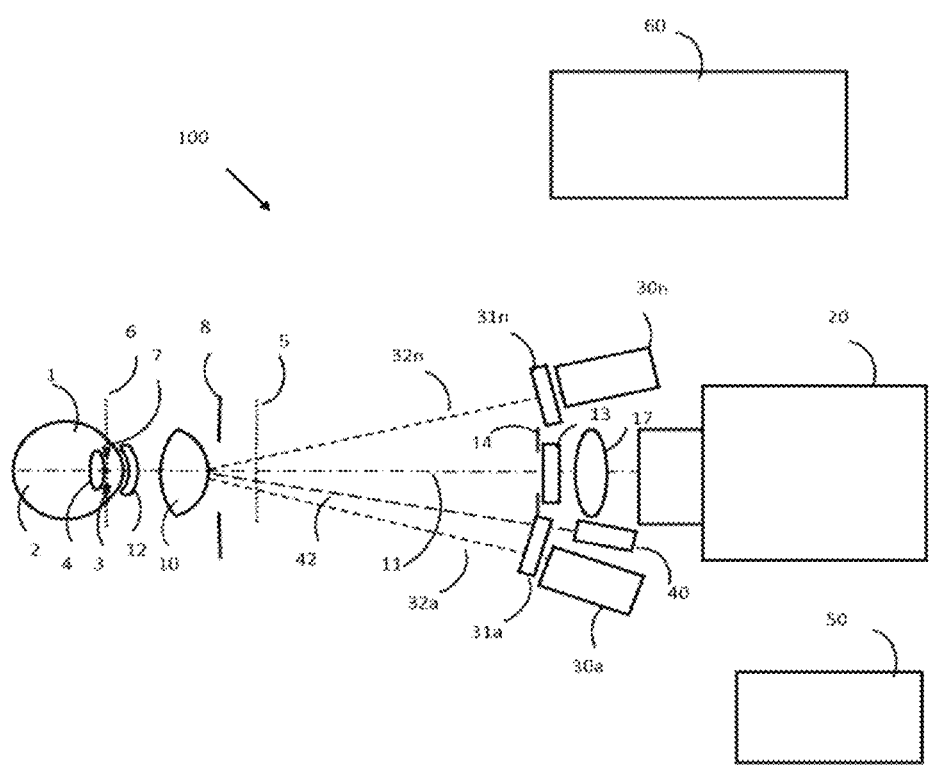
FIG. 2 shows an illustrative example of a wide field fundus camera implemented using multiple illumination beam projectors and a narrow beam projector.

FIG. 2 shows an illustrative example of a wide field fundus camera 100 with multiple illumination beam projectors 30a-30n and a narrow beam projector 40. The wide field fundus camera 100 includes primarily an objective lens 10, an image recording device 20, a plurality of illumination beam projectors 30a-30n, a narrow beam projector 40, a first polarizer 13 and a set of second polarizers 31a-31n. The wide field fundus camera 100 further includes a contact lens 12, a focusing lens 17, an electronic controller 50 and an image display 60.

Objective lens 10 may be an aspherical lens and is located at a first end of the wide field fundus camera 100. The objective lens 10 defines a symmetric viewing axis 11 and a working plane 6 of the wide field fundus camera 100. The plurality of illumination beams 32a-32n emerging through an illumination aperture 8 are pre-focused at the working plane 6. When a subject eye 1 is aligned with the wide field fundus camera 100 for fundus viewing, subject pupil 3 is about to position at the working plane 6 and the illumination beams 32a-32n are projected into subject pupil 3 to illuminate the subject retina 2 for alignment and for photographing. At a proper alignment, objective lens 10 produces a first retina image near its back focal plane 5, and the first retina image is then re-imaged into the image recording device 20. The illumination aperture 8 is located at the back focal plane 5 so as to define illumination area on the subject retina 2.

At a proper alignment, objective lens 10 also forms an image of the subject pupil 3 onto the plane of optical stop 14, which thus defines a small, virtual viewing window on the subject pupil 3 for the camera 20 to look through into the retina 2. The illumination beams 32a-32n are thus respectively focused at the subject pupil 3, and the focal spots are pre-positioned outside the virtual viewing window. Therefore, any scattering light of illumination beams 32a-32n scattered outside this virtual viewing window will be substantially blocked from getting into the image recording device 20.

In an illustrative example, the wide field fundus camera 100 may provide a static field of view of 120 degrees or wider on the subject retina 2. In this illustrative example, the objective lens 10 has an optical power of about 120 D and a diameter of about 18 mm. The objective lens 10 has thus a back focal length of shorter than 8 mm and a small working distance of approximate 4 millimeters with respect to the subject cornea 7. The objective lens 10 may be an aspherical lens such that to have relative lightweight and to produce optimal image quality over the subject retina 2.

A contact lens 12 may be positioned in front of the aspherical objective lens 10 and in direct contact with the subject cornea 7. The contact lens 12 may or may not have optical power. FIG. 2 shows how a contact lens 12 is incorporated with the aspherical objective lens 10 to produce a first retinal image of the retina 2. In an illustrative example, the contact lens has a diameter of about 10 mm to fit for the small eyeball 1 of infants.

There are commercially available aspherical lenses for retinal viewing, with indirect ophthalmoscopes or slit lamp microscopes. For instance, an aspherical lens integrated with a contact lens can be found in an Ocular ORMR-2x (Ocular Instruments, Bellevue, Washington, United States of America).

The image recording device 20 is located at a second end of the wide field fundus camera 100 and is to view and to photograph fundus image through objective lens 10. Also, this image recording device 20 is in an illustrative example able to perform auto-focusing and auto-exposure control. The image recording device 20 in an illustrative example may include a consumer image recording device that includes advanced features of autofocus, auto exposure, real-time display, and image storage and transfer, and that is compact, lightweight, and easy to use. The image recording device 20 may have a built-in function to readily transfer its recorded image to a local computer or another processor for internet connectivity and telemedicine networks. The image recording device 20 as an illustrative example may have a resolution over two megapixels and have an entrance pupil of 8 mm or bigger to receive all light passing through the optical stop 14. The image recording device 20 may have a feature of a custom setting and be capable of saving working parameters for convenient operation. The image recording device 20 may have a separate display 60 for easy viewing, to provide a desirable viewing angle, display size, and display distance.

The image recording device 20 in an illustrative example is a smart lens type of consumer camera, such as a Sony QX100 (Sony Corporation, Japan). In this illustrative example, the image recording device 20 is coupled to the display 60 via Wi-Fi, and the display 60 may be a wireless device such as an iPhone or an iPad. Also, this image recording device 20 may have high sensitivity and high-resolution operation.

The plurality of illumination beam projectors 30a-30n may include two or more illumination beam projectors 30a-30n. Each of the projectors 30a-30n projects an illumination beam 32a-32n at an angle toward the objective lens 10. In an illustrative example, each illumination beam 32a-32n has a small vergency and has a beam size to cover the illumination aperture 8. This way, each illumination beam 32a-32n is to mimic the illumination of an indirect ophthalmoscope and to illuminate a portion of an image on the subject retina 2. In an illustrative example, the plurality of illumination beam projectors 30a-30n produces four illumination beams 32a-32n, of which each illuminates a quadrant of the field of view on the subject retina 2.

A wide field fundus camera 100 may be operated in the mydriatic condition, and white light illumination can be used for both aligning and photographing the subject retina 2. In an illustrative example, each of the plurality of illumination beam projectors 30a-30n includes a high brightness, high power white LED and a projection lens to produce a white light illumination beam 32a-32n. The white light LED may include a warm white light source with a color temperature about 3000 degrees Kelvin. For radiation safety, each illumination beam 32a-32n is limited to project a few milli-watts of illumination power.

When another illumination condition is desirable, the illumination beam projectors 30a-30n can include one or more of high power, high brightness infrared LEDs. Further, the illumination beam projectors 30a-30n can include one or more of high power, high brightness LEDs capable of projecting a limited spectral range of illumination such as red, green, or blue light.

The projection angle of the illumination beams 32a-32n may be set so as to move corneal and crystalline lens reflections away from the central viewing area. On the other hand, the projection angle of the illumination beams 32a-32n is limited to the minimum pupil size that the wide field fundus camera 100 is intended to use. For screening for ROP, the minimum pupil size is set to approximately 5 mm, and the projection angle of the illumination beams 32a-32n is thus set to about 10 to 15 degrees.

The narrow beam projector 40 is to project a narrow illumination beam 42 and to form a bright illumination feature on the retina 2 to facilitate auto focusing of the image recording device 20. Typically, a consumer image recording device 20 requires a relatively high illumination level and a relatively high contrast target feature to obtain reliable and effective auto focusing. A bright and narrow slit beam illumination on or near the center of retina 2 is illustrated. In one illustrated example, the dimensions of the slit beam are about 3 mm long and 1 mm wide on the retina 2.

The narrow illumination beam 42 is to project at an angle with respect to the viewing axis 11. In an illustrative example, the narrow slit beam 42 is focused outside the virtual image window and has no overlap with the image beam path throughout the crystalline lens 4.

The first polarizer 13 and the set of second polarizers 31a-31n may form a cross-polarization condition to reject specular reflections of the illuminations beams 32a-32n back into the image recording device 20. For a predetermined orientation of the first polarizer 13, each of the second polarizers 31a-31n may be rotationally adjusted to form a precise condition of cross polarization. Specular reflections at surfaces of the objective lens 10 and contact lens 12 are particularly strong and necessary to remove. Specular reflections from the first corneal surface (i.e. first Purkinje reflection), the first surface of the crystalline lens (i.e., third Purkinje reflection) and the second surface of the crystalline lens (i.e., fourth Purkinje reflection) can be a major source of image haze. A high extinction ratio of cross polarization is required for reflection haze reduction. The polarizers 31a-31n and 13 may be selectively thin film polarizers and have an extinction ratio of 300 or higher throughout the visible and infrared light spectrum.

The contact lens 12 may serve as an optical window of the wide field fundus camera 100 to interface with the subject cornea 7. The contact lens 12 is illustrated to have an anti-reflection coating on its convex surface. As the illumination beams, 32a-32n and the narrow illumination beam 42 are small and bright on the contact lens 12, effort is required to minimize and to remove specular reflection from its convex surface that interfaces to air.

The focusing lens 17 in one illustrative example is an achromatic lens with a focal length about 60 mm to 80 mm and is positioned one focal length away from the back focal plane 5 of the objective lens 10. In one illustrative example, the collimation lens 17 is to reimage the first retinal image formed by the objective lens 10 into distance, and thus the image recording device 20 is operated to focus at distance. This way, the focal length of camera 20 can be adjusted continuously to match a desirable field of view, and the selected retinal image area can thus fill up the camera display 60. As a result, the pixel resolution of the camera and its display can be optimized. Focusing lens 17 and objective lens 10 may form an optical afocal relay, to relay the outgoing beam from the subject pupil 3 to the image recording device 20. The optical afocal relay has a scaling factor m, equal to the ratio of the focal lengths between the focusing lens 17 and the objective lens 10. In an illustrative example, the focusing lens 17 has a focal length of 60 mm, and the optical afocal relay has a scaling factor m of about 7.5.

Optical stop 14 may be positioned in front of the image recording device 20 and is conjugated with the working plane 6 of the wide field fundus camera 100 via objective lens 10. The optical stop 14 has an aperture corresponding to a predetermined virtual viewing window on the subject pupil 3. For instance, for a scaling factor of 7.5 and a virtual viewing window of 1.3 mm on the subject pupil 3, the optical stop 14 is thus 10 mm. In operation, the subject pupil 3 is aligned with the working plane 6, and the optical stop 14 blocks any light scattered from outside the virtual viewing window on the subject pupil 3. The aperture of the optical stop 14 may also be limited to the effective aperture of the image recording device 20.

The electronic controller 50 is to couple with the image recording device 20 and to power the illumination projectors 30a-30n and the narrow beam projector 40. In an illustrative example, the electronic controller 50 powers the illumination projectors 30a-30n at a low power level during alignment and then ramps up them to a high power level for photographing the subject retina 2. The power level of each of the illumination projectors 30a-30n can be controlled in a programmable manner. This way, the illumination projectors 30a-30n can be synchronized with the image recording device 20 to take multiple retinal images with various on-off configurations and time sequences.

The display 60 may couple with and display real-time images of the image recording device 20. In an illustrative example, the display 60 is a high definition monitor and is coupled wirelessly to the image recording device 20. For instance, the image recording device 20 may be a Sony QX100 (Sony Corporation, Japan) and the display may be an iPad (Apple, Cupertino, California, United States of America) and data transfer between the two devices may be through Wi-Fi built into the devices.

The images captured by the image recording device 20 may be stored in the camera 20, monitored at the display 60, and transferred to a local computer or other networked computers. The images captured by the image recording device 20 may thus be viewed through the network, and retinal diseases can be diagnosed by a retinal professional in a local or remote location.

A digital controller 50 may be used to independently control each illumination beam projector 30a-30n. In an illustrative example, there are four independent LED beam projectors controlled by a digital controller. The controller may be connected to a tablet through its USB port, and the user interface to the image recording device 20 and the digital controller 50 may be provided on the tablet display.

Figure 8:
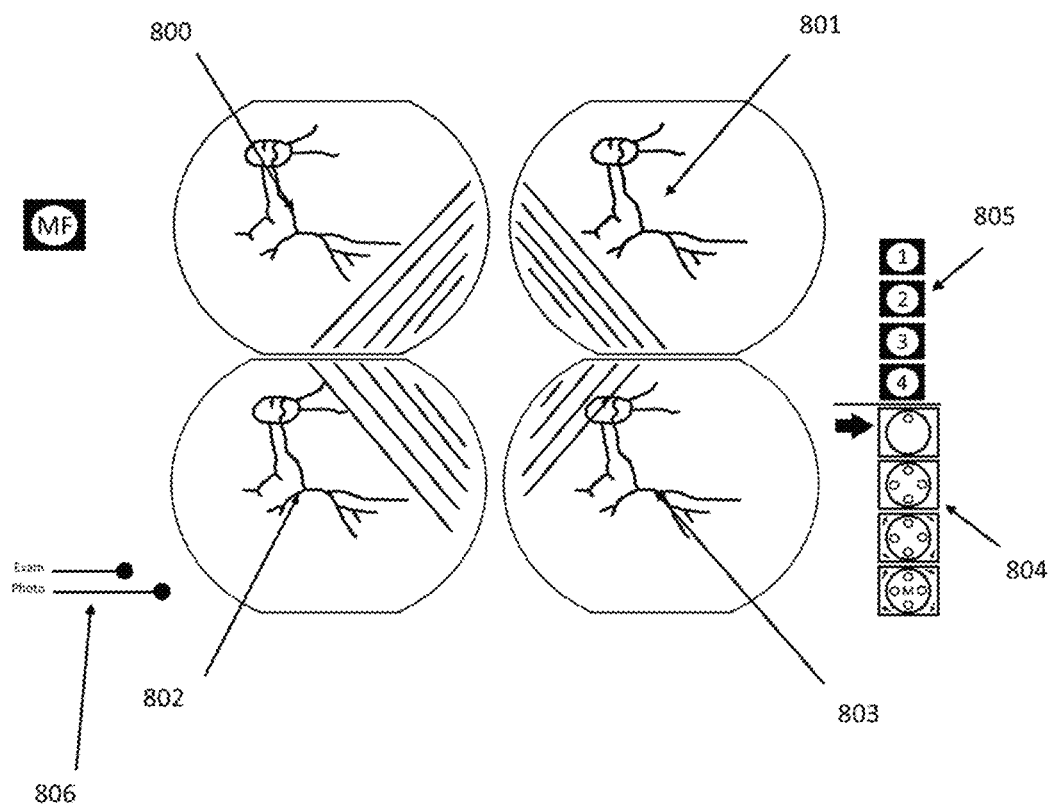
FIG. 8 shows an illustrative example of the tablet display demonstrating real-time live view display of the retinal image formed by four independent projector beams that may allow proper user alignment with the eye. Additionally, user controls to set real-time illumination level, photo flash illumination level, the pattern of independent projector beam illumination control, and independent manual control of each projector beam are shown.

In FIG. 8, an illustrative example demonstrates how the user can control each of the four independent beam projectors 30a-30n and turn each one on or off via an illumination pattern selector 804. The independent beam projectors 30a-30n may also be serially programmable, and the pattern, timing, and beam illumination intensity can be controlled by the user via an illumination mode selector 805. The power level for each independent beam projector 30a-30n may be controlled for both real-time live-view imaging of the retina, as well as flash photography via an illumination level adjustor 806. For flash photography, the illumination beam projectors 30a-30n may be temporarily adjusted to a higher intensity than in live-view imaging mode, for the purpose of final photo acquisition or auto-focusing purposes. Rapid sequential serial illumination control of each independent beam projector 30a-30n may allow the retinal view provided by each independent beam projector to be shown simultaneously in separate live-view images of the retina 800, 801, 802, 803. For example one of four independent illumination beam projectors 30a-30n can be individually turned on and the retinal image resulting from each of four independent beams then shown in four separate panels on the same display 800, 801, 802, 803. In an illustrative example, each independent beam projector 30a-30n may be turned on for less than 100 ms, serially turning on each beam projector 30a-30n one at a time, allowing acquisition of the views provided by each of the four independent beam projectors in less than 400 ms. This timing can prevent lag in the live-view and allow the user to align the camera with the eye to optimize illumination provided by each independent beam projector 30a-30n.

Figure 10:
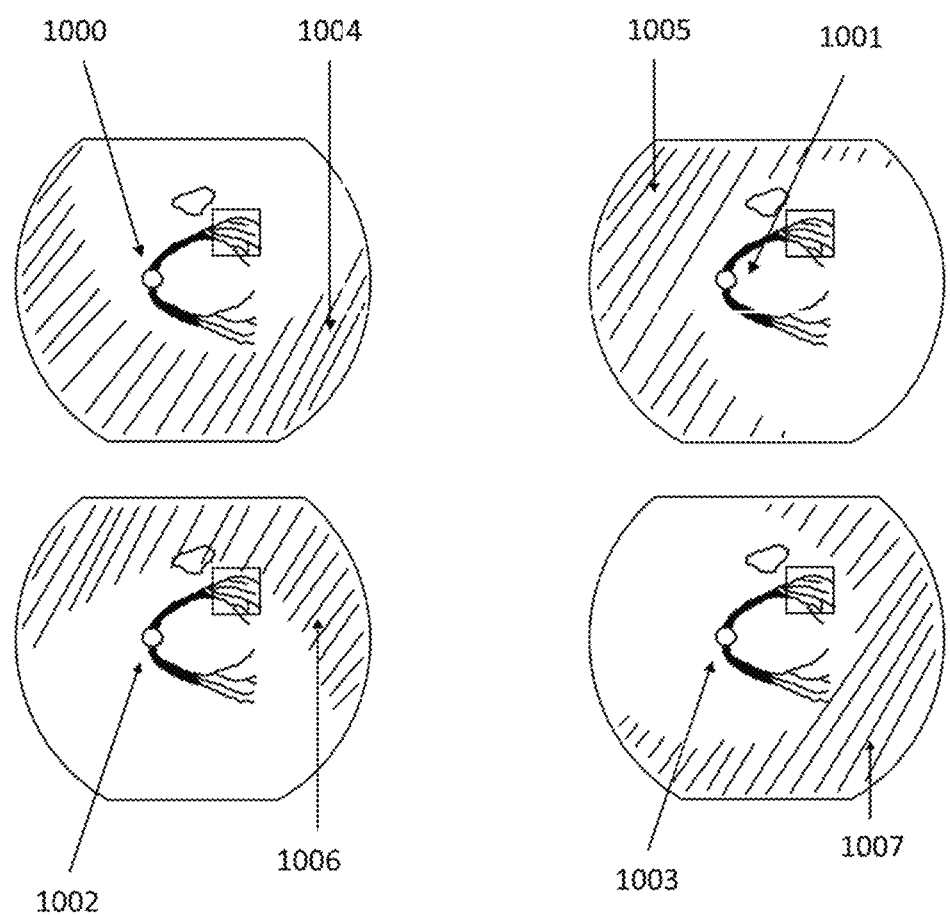
FIG. 10 shows an illustrative example of the live-view display formed by the electronic controller and image recording device at four different points in time. At each point in time, a single independent projector beam may be illuminated, with each of four separate independent projector beams illuminated serially as shown in the four panels. The display would appear to the user real-time as a rotating illumination beam that may allow the user to assess alignment of each illumination projector beam with the eye before final image acquisition.

In a separately illustrated example in FIG. 10, a single live view image of the retina may be provided, and each independent beam projector 30a-30n can be turned on and then off for a discrete period of time. Said beam projectors turn on rotating clockwise or in another programmed manner, one or more projector beams at a time, to allow the user to see the illumination provided by each beam projector for assessing alignment of the camera with the eye prior to final retinal image acquisition. For example, one of four independent beam projectors 30a-30n may be turned on for 250 ms 1000 and then turned off. Then the next independent beam projector is turned 1001 on for 250 ms and then turned off. Then the next independent beam projector is turned 1002 on for 250 ms and then turned off. Then the next independent beam projector is turned 1003 on for 250 ms. This sequence of beam illumination control could be repeated until a final retinal image is acquired. The four panels shown in FIG. 10 1000, 1001, 1002, 1003 provide an example display seen at four different points in time and would appear to the user as a rotating beam in real-time. Each independent beam projector 30a-30n may create a clear quadrant of viewing of the retina 1000, 1001, 1002, 1003 as well as an area of lens haze and reflections 1004, 1005, 1006, 1007 due to scattering of the illumination beam in objective lens 10, and the human lens 4.

A method may be used to process the multiple retinal images provided by each independent projector beam 30a-30n and to stitch them into a single fundus image. An illustrative example of this method is a processor circuit coupled to a memory circuit, the memory circuit including instructions that cause the processor circuit to receive imaging information corresponding to the plurality of retinal images and to provide a composite image including stitching together the plurality of retinal images into a single montage image. Please refer to FIG. 9. In an illustrative example, a plurality of retinal images is acquired for four independent beam projector 30a-30n, turned on sequentially one at a time with the separate acquired retinal images shows as 900, 901, 902, and 903. Image haze from the specular reflections from the human lens is evident in each image and is indicated by 906, 907, 908, and 909. The portion of each image without human lens haze 900, 901, 902, 903 using said method can be stitched together to form a final montage image 905. Blending may be performed on the separate images that form the final montage to eliminate seams and even exposure across the final montage. The method used to process said multiple retinal images may also identify the human lens haze (906, 907, 908, 909), for illustrative example by both its contrast level and characteristic position based on which independent illumination projection beam is on and the angle the projection beam has with the eye. This haze may be masked by said image processing method before performing the final montage.

Figure 3:
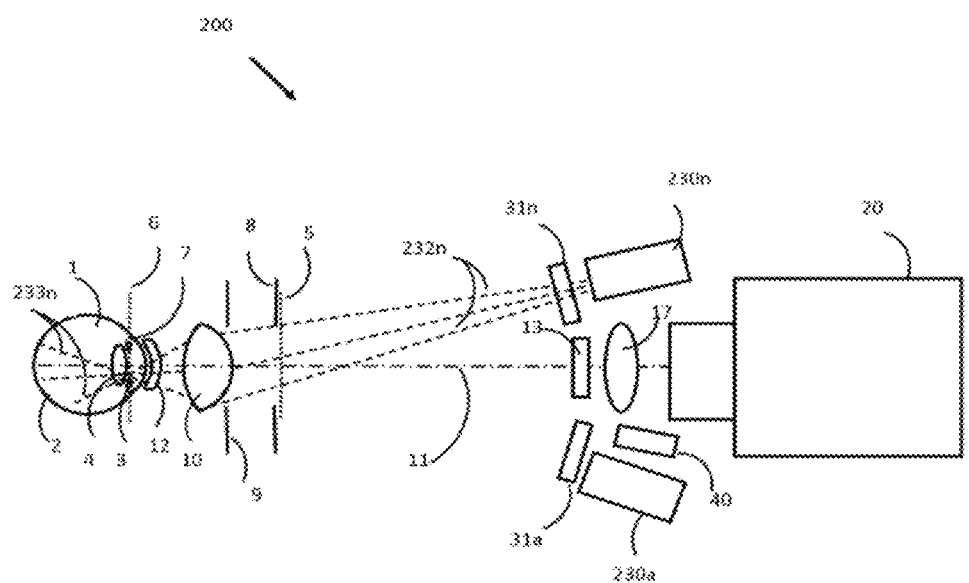
FIG. 3 shows an illustrative example of a wide field fundus camera having one of the multiple illumination beam projectors turned on for taking one of the multiple retinal images.

FIG. 3 shows an illustrative example of a wide field fundus camera 200 having an illumination beam projector 230n turned on for taking one of the multiple retinal images. The illumination beam projector 230n projects an illumination beam 232n onto the objective lens 10 at an angle with respect to the viewing axis 11, mimicking the illumination configuration of an indirect ophthalmoscope. The illumination beam 232n is then focused on the working plane 6 and directed into subject pupil 3. This illumination beam 232n passes through the subject pupil 3 and turns into illumination beam 233n to illuminate subject retina 2.

Because the illumination beam 232n is projected at an angle and is shaped by the apertures 8 and 9, the illumination beam 232n can thus be focused into subject pupil 3 and be away from the pupil center. In an illustrated condition, the illumination beam path is not overlapped with the image beam path inside the crystalline lens 4, and scattering light scattered from the crystalline lens 4 is not captured by the image recording device 20. In this way, image haze resulting from lens scattering of the illumination beam inside a less-transparent crystalline lens may be significantly reduced.

Also, because the illumination beam 232n is projected at an angle and is shaped by the apertures 8 and 9, the illumination beam 233n is not symmetric on the subject retina 2. More than a quadrant of the field of view may be illuminated via such an illumination configuration. At this illumination condition, an image captured by the image recording device 20 may show only a portion but not the full field of view being illuminated. Therefore, multiple images may be required to capture the subject retina 2 to have a full field of view. In an illustrative example, four illumination beam projectors 230 are used and four retinal images may be captured in time sequence to provide a 120-degree field of view of the subject retina 2.

Figure 3B:
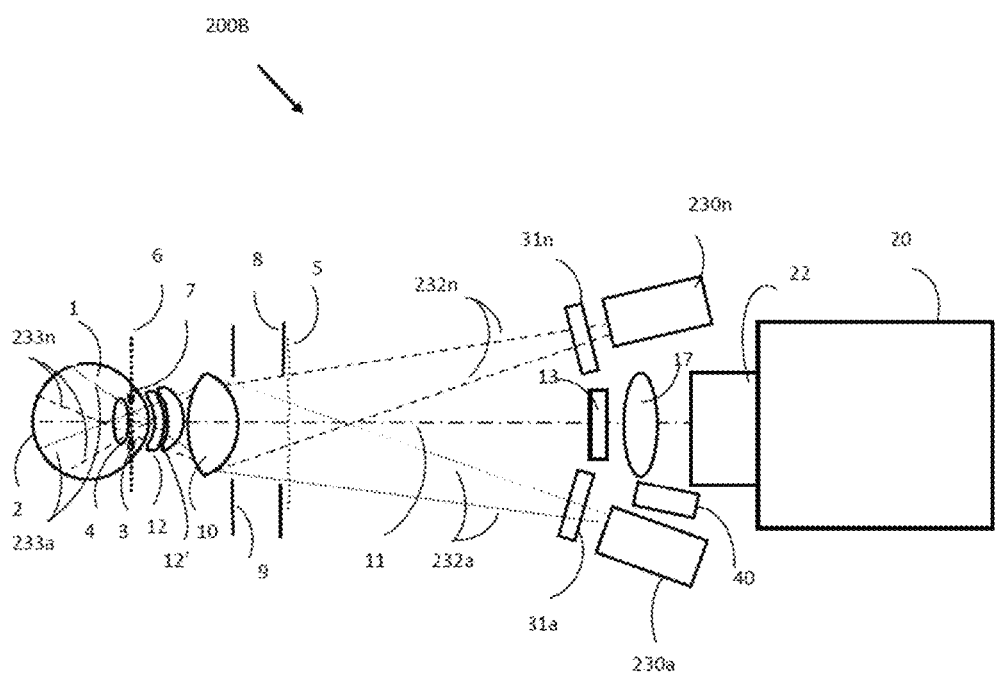
FIG. 3B shows an illustrative example of an ultra-wide field fundus camera modified from FIG. 3 that uses an ultra-wide FOV lens. The wide-field FOV lens in FIG. 3 has been replaced with an ultra-wide FOV lens comprised of a meniscus, contact, and objective lens allowing visualization of greater than 160-degree FOV of the retina.

FIG. 3B shows an illustrative example of an ultra-wide field fundus camera 200B modified from FIG. 3. A meniscus lens 12' is inserted in between the contact lens 12 and the objective lens 10 to form an ultra-wide field objective lens including the contact lens 12, the meniscus lens 12' and the objective lens 10. Preferably, the contact lens 12 is formed with a plastic contact element of low diopter power, and the meniscus lens 12' is a glass lens of much higher diopter power. The objective lens 10 can be an aspherical lens and can be aspherical on both front and back surfaces to correct optical aberrations for the ultra wide field of view.

In a preferable symmetric configuration of the illumination beams, 4 or 8 illumination beam projectors 230 are used to provide axial symmetric illumination with respect to the instrument axis 11. In a preferable operation procedure, two or four illumination beams 232a-232n can be used to produce central symmetric illumination beams 233a-233n on the retina when the instrument axis 11 is aligned with the eye optical axis. Once such an on-axis alignment is achieved, the reflection spots from the contact lens surfaces and the ocular surfaces and the scattering haze from the cornea 7 and crystalline lens 4 are distributed symmetrically on the retinal image (e.g. photo image 1100a). Consequently, the reflection spots and scattering haze can be used to guide the centration and axial alignment of the fundus camera 200B toward a symmetric distribution with respect to the image center.

Figure 4:
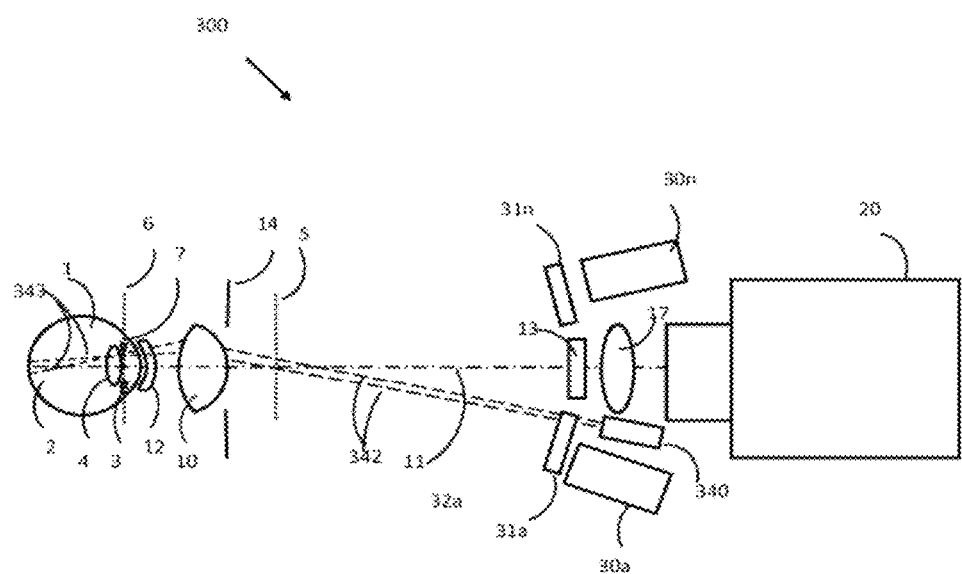
FIG. 4 shows an illustrative example of a wide field fundus camera having the narrow beam projector turned on to facilitate autofocusing through less transparent crystalline lens and reflection haze.

FIG. 4 shows an illustrative example of a wide field fundus camera 300 having the narrow beam projector 340 turned on to facilitate autofocusing through less transparent crystalline lens 4 and reflection haze. The narrow beam projector 340 is to project a narrow illumination beam 342 and to form a bright illumination feature on the subject retina 2. A consumer image recording device 20 may require a relatively high illumination level and a relatively high contrast target feature to obtain reliable and effective auto focusing. In particular, a bright and narrow slit beam illumination on or near the center of the subject retina 2 may be favorable for such autofocusing. In one illustrated example, the dimensions of the slit beam are about 3 mm long and 1 mm wide on the subject retina 2.

The narrow slit beam 342 can be projected at an angle with respect to the viewing axis 11. In an illustrative example, the narrow slit beam 342 is focused outside the virtual image window and has no overlap with the image beam path throughout the crystalline lens 4. This way the slit beam image on the image recording device 20 is not blurred by scattering light from the crystalline lens 4, and the narrow slit beam 342 thus serves to facilitate autofocusing through less transparent crystalline lens 4.

Figure 5:
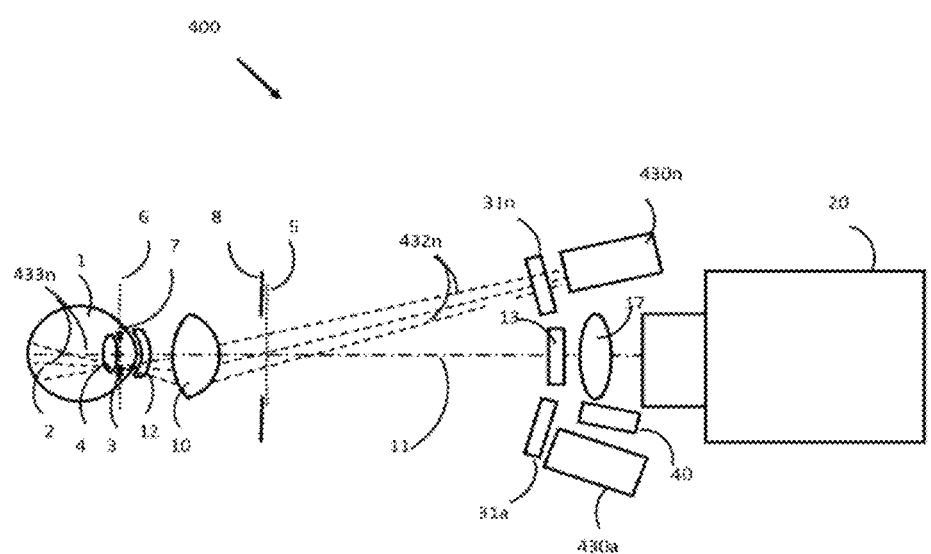
FIG. 5 shows an illustrative example of a wide field fundus camera having one of the multiple slit beam projectors turned on to improve image taking through less transparent crystalline lens and reflection haze.

FIG. 5 shows one illustrative example of a wide field fundus camera 400 having one slit beam projector 430n turned on to improve image taking through less transparent crystalline lens 4 and reflection haze. The slit beam projector 430n projects a slit beam 432n toward the objective lens 10, in which the slit beam 432n has a narrow dimension in the incident plane of the illumination and a full dimension normal to the incident plane. As shown in FIG. 5, such a slit beam 432n turns into a slit illumination beam 433n on the subject retina 2. Also, such a slit beam 432n is confined away from the viewing axis 11 and thus may have a better clearance with the image beam path inside the crystalline lens 4. Consequently, an overlapping region between the illumination beam path and the image beam path can be avoided inside the crystalline lens 4, and thus image haze due to light scattering inside less transparent crystalline lens 4 may be substantially improved.

In an illustrative example, the slit beam 432n of FIG. 5 may provide a retinal slit image of approximately 60 degrees in the narrow dimension and 120 degrees in the length dimension, i.e., a dimension normal to the incident plane of the page. In one illustrative example if such a retinal slit image is taken at a rotational angle of 60 degrees separate from each other, then three of such retinal slit images may cover the full image of the subject retina 2. In an illustrative example, three slit beam projectors 430a-430n are positioned 120 degrees from each other around the symmetric viewing axis 11, and each projects a slit beam 432n with its narrow dimension orientated in its own incident plane. In this case, three retinal images may be taken to form a complete full field of view of the subject retina 2. Similarly, in another illustrative example if the slit beam narrow dimension is about 40 degrees, five of slit beam projectors 430a-430n may be used, and five slit beam images may be taken to cover a full field of view of the subject retina 2 with the objective lens 10.

Figure 6:
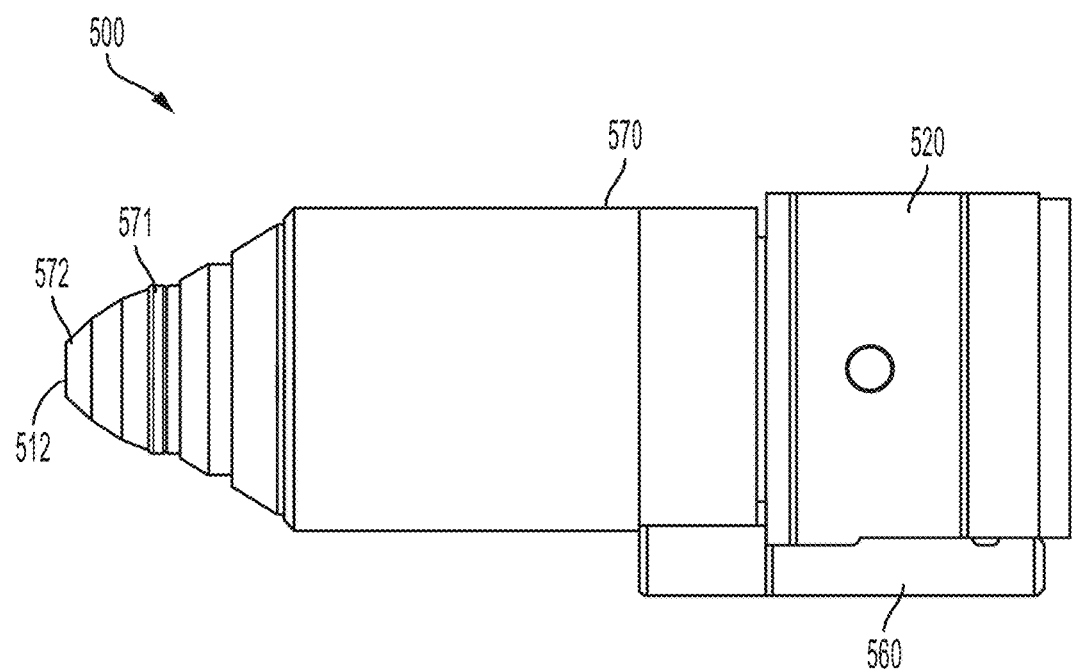
FIG. 6 shows an illustrative example of a handpiece that integrates the multiple illumination projectors, the imaging optics, a consumer image recording devices and the contact lens of the wide field fundus camera.

FIG. 6 shows an illustrative example of a handpiece 500 that integrates a central housing 570 for the multiple illumination projectors, a front housing 571 for the objective lens, an image recording device 520 and a contact lens 512 of the wide field fundus camera. In this illustrated example, the image recording device 520 is a Sony QX100, and it is affixed to the central housing 570 via a mechanical coupler 560. The contact lens 512 may be mounted on a contact lens holder 572, which is attached to the front housing 571. This way the contact lens 512 may be removed with the holder 572 for easy sterilization.

In one illustrative example, the handpiece 500 may have an elongated shape, having dimensions about 60 mm in diameter and 200 mm long. In another illustrative example, for screening for ROP, the front end of the handpiece 500 is about 10 mm in diameter.

Figure 7:
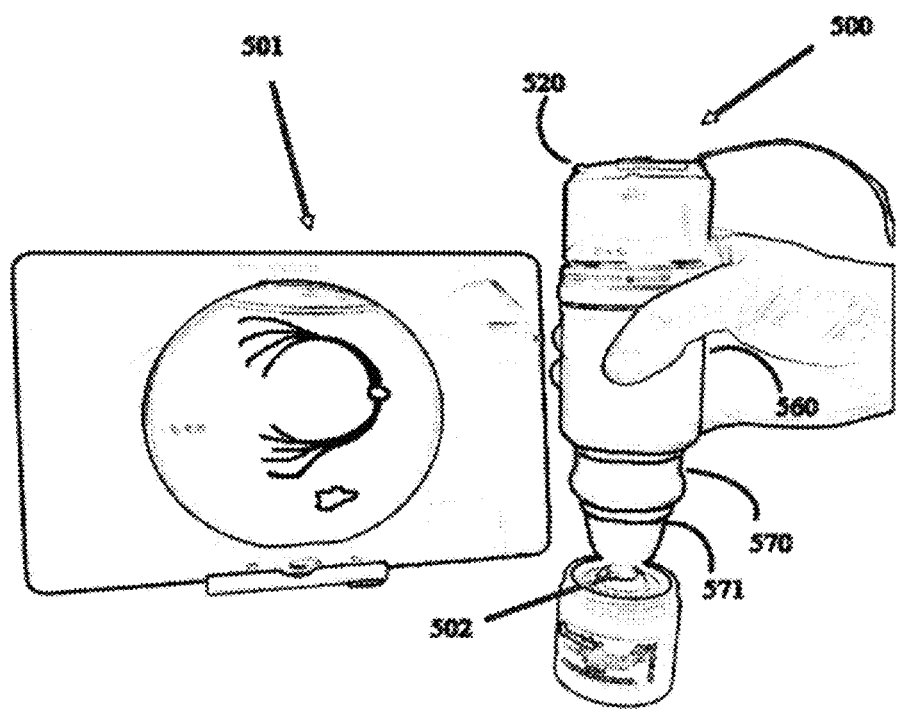
FIG. 7 shows an illustrative example handpiece with Olympus Air A01 consumer image recording device placed on a model eye and the resulting retinal image taken by the wide field fundus camera projected wirelessly over to a tablet.

FIG. 7 shows an illustrative example of a handpiece 500 that integrates a central housing 570 for the multiple illumination projectors, a front housing 571 for the objective lens, an image recording device 520 and a contact lens 512 of the wide field fundus camera. In this illustrated example, the image recording device 520 is an Olympus Air A01 (Olympus Corporation, Japan) and it is affixed to the central housing 570 via a mechanical coupler 560. In one illustrative example, images from the image recording device 520 may transmit via Wi-Fi to a tablet display which in this illustrated example is a Samsung Galaxy Note 501

FIG. 8 shows the tablet display for one illustrated example of the electronic controller. In this example, four independent illumination beam projectors are controlled by the electronic controller. The electronic controller serially may turn on each illumination beam projector one at a time, and the image recording device 520 may capture an image with each illumination beam. 801 shows the first illumination projector beam turned on with all other beams turned off, 802 shows the second illumination projector beam turned on with all other beams turned off, 803 shows the third illumination projector beam turned on with all other beams turned off, 800 shows the fourth illumination projector beam turned on with all other beams turned off. For example, the total time to turn on and off each of the four independent beams may be less than 400 milliseconds, with 100 milliseconds for each beam. Said process may allow a real-time display of how the retinal image formed by each independent beam will appear to assess alignment of each independent beam projector with the eye. The pattern of serial illumination control of each independent beam projector may be controlled by the user and may be programmable by selecting one of four possible patterns 804. Each independent beam projector may be manually and independently turned on and off through a separate user control 805. Power levels for each independent illumination projection beam may be controlled by the user both for real-time live examination and flash photography level when the final photo is captured by the image recording device 806.

Figure 9:
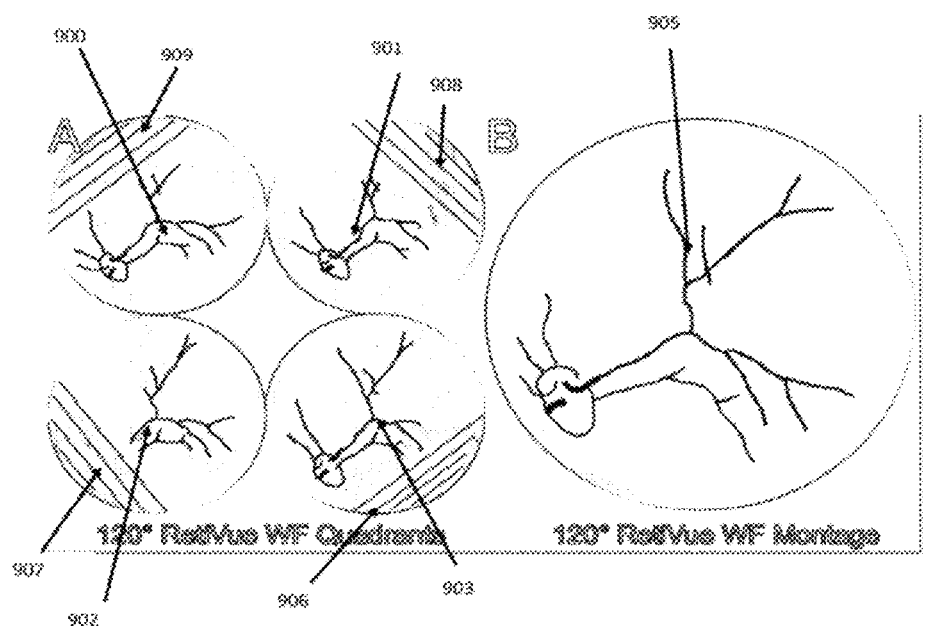
FIG. 9 shows an illustrative example of the separate retinal images formed by each of four independent projector beams. An image processing method may be used to eliminate the lens reflection haze from each projector beam and stitch together the clear aspect of the retinal image to form a final seamless montage that is adjusted to achieve even exposure across the final montaged image.

FIG. 9 shows one possible illustrated example for a method of image stitching of the plurality of images taken by independent illumination projector beams. In this example, four retinal images are taken, each having one of four independent beam projectors turned on. 901 shows the first illumination projector beam turned on with all other beams turned off, 902 shows the second illumination projector beam turned on with all other beams turned off, 903 shows the third illumination projector beam turned on with all other beams turned off, 900 shows the fourth illumination projector beam turned on with all other beams turned off. Each independent beam projector may create a specular white reflection and haze 906, 907, 908, 909, from the human lens of the eye 4 and the objective lens 10, but also illuminates a quadrant of the retina without lens haze 900, 901, 902, 903. The image processing method may remove the area in each illumination projector beam image where there is lens haze from the human lens 906, 907, 908, 909, and join the portion of each illumination projector beam image without lens haze 900, 901, 902, 903. Blending may be performed on the stitched pieces to seamlessly blend differences in exposure level of each illumination projector beam image. The final montage 905 may eliminate the lens haze 906, 907, 908, 909 from the montaged image. The image processing method may include a processor circuit coupled to a memory circuit, the memory circuit including instructions that cause the processor circuit to receive imaging information corresponding to the plurality of retinal images and to provide a composite image including stitching together the plurality of retinal images into a single montage image. It may further include a processor circuit coupled to a memory circuit, the memory circuit including instructions that cause the processor circuit to receive imaging information corresponding to the plurality of retinal images and remove artificial reflection spots and lens haze from each of said plurality of retinal images.

Figure 11A:
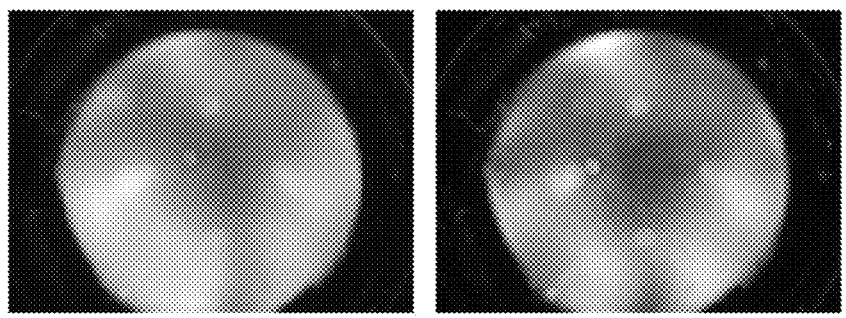
In FIG. 11a no haze removal has been performed.

FIG. 11 shows an illustrative example of an ultra-wide FOV image of a baby eye 1100a taken with a wide-field fundus camera using an ultra-wide FOV lens according to FIG. 3B. FIG. 11a shows four illumination beam projectors 230n, 230a positioned at 12, 3, 6, and 9 o'clock about the central viewing axis 11 that illuminate the retina 2 to provide an ultra-wide FOV image of the retina 1100a. The ultra-wide FOV image of the retina 1100a is processed using an illustrative example of a real-time dehazing algorithm to generate a dehazed ultra-wide FOV image of the retina 1100b. Four illumination beams 230n, 230a are used and four reflection spot clusters 1102-1105 are symmetric with respect to the center of the retinal image 1101a. The reflection haze pattern is also substantially symmetric with respect to the center of the retinal image 1101a. Each reflection spot cluster may include visibly two or more reflection spots 1102a from the contact lens 12, the cornea 7 (Purkinje I and II) and the crystalline lens 4 (Purkinje III and IV) and scattering haze spot from the corneal tissue and lens 1106a. In an alignment shown in photo image 1100a, the four reflection spot clusters 1102-1105 are located at 12, 3, 6, and 9 o'clock positions, because the four illumination beam projectors are orientated at x and y positions with respect to the instrument axis 11 of wide field fundus camera 200B. During an alignment process, the locations and movements of these reflection spots can be used as indicators to guide instrument alignment to obtain alignment of the wide-field fundus camera FIG. 3B, with the central axis of the eye 11.

Figure 11B:
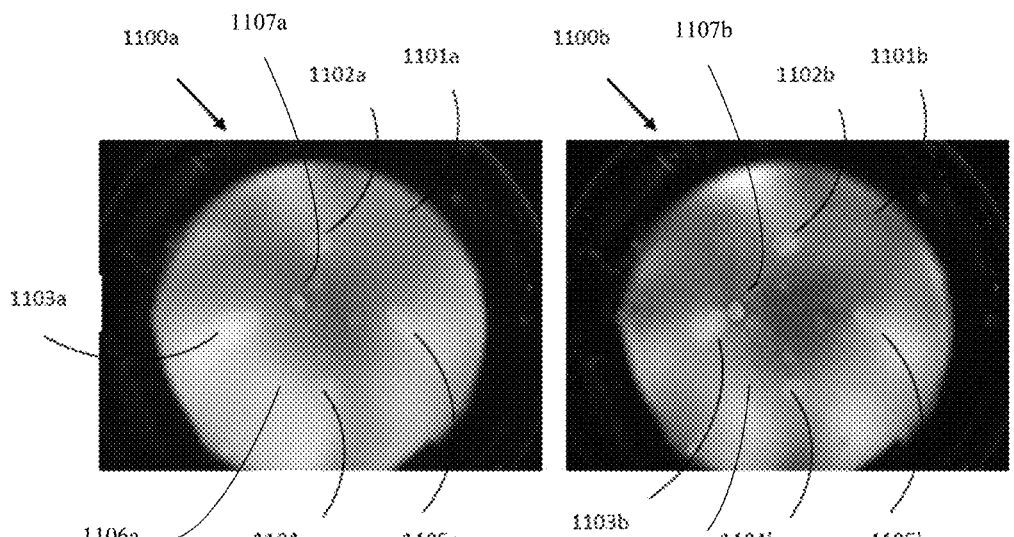
In FIG. 11b one embodiment of real-time dehazing has been used to partially remove reflected and scattering haze to enhance visualization of retinal detail.

FIG. 11b shows the same photo image 1100b as shown in 1100a, following further processing of said photo image 1100a using an illustrative example of real-time dehazing to generate a dehazed image 1100b. Comparing to photo image 1100a, photo image 1100b demonstrates more retinal details to enable better judgment on alignment of wide field fundus camera 200B and focus of retina 2 on wide field fundus camera sensor 20.

Real-time dehazing is a computer function implemented in a processor circuit associated with the fundus camera 200B of FIG. 3B to reduce image haze in a real-time manner, generating a dehazed image in one illustrative example in less than 200 milliseconds. The processor circuit can be a high-speed computing processor, e.g. a high-speed laptop computer. The computing processor is coupled with the camera to enable real-time image processing and display. Real-time dehazing can be accomplished in one illustrative example by computing the estimated haze map using at least one of reference spectrum and size and spatial distribution of said reflected and scattering haze, computing the transmission map utilizing estimated haze map for said wide field fundus image, refining the transmission map utilizing estimated retinal transmission from a reference retinal wide field fundus image, to produce a dehazed retinal image.

In one illustrative example, selection of elements comprising an ultra wide-field fundus camera lens (10, 12', 12) and design of illumination beam projectors 230*n*, 230*a*, allows simultaneous visualization of Purkinje reflections 1102*a*-1105*a* and retinal image (ie optic nerve 1107*a*) details. In this illustrative example, this is enabled by projection angle of 12 degrees for said illumination beam projectors, use of a 160-degree field of view ultra-wide field lens, with aspherical curvature and field of view sufficient to visualize said Purkinje reflections within the FOV, and wide field fundus camera lens 20 with depth of field sufficient for simultaneous visualization of Purkinje reflections and retina within said ultra-wide FOV image. Purkinje reflections 1102*a*-1105*a* and retinal image (ie optic nerve 1107*a*) details can be used to guide alignment of said wide field fundus camera 200B with the retina 2. Real-time dehazing of the wide field fundus image can reveal additional retinal details 1106*b*, enhance appearance of retinal structures such as the optic nerve 1107*b*, and enhance appearance of the Purkinje reflections 1102*b*-1105*b* to facilitate alignment of the wide field fundus camera 200B with the retina 2.

FIG. 12 shows an illustrative example of two sequential photo images 1200*a* and 1200*b* captured by the ultra-wide field fundus camera 200B of a baby eye. FIG. 12*a* shows a retinal image 1200*a* captured by said wide field fundus camera 200B using two illumination beam projectors 230*n* positioned at 3 and 9 o'clock around the central viewing axis 11. FIG. 12*b* shows a retinal image 1200*b* captured by said wide field fundus camera 200B using two illumination beam projectors 230*n* positioned at 12 and 6 o'clock around the central viewing axis 11.

In photo image 1200*a*, the reflection spot clusters 1203*a* and 1205*a* are aligned horizontally to center with retinal image 1201*a*, and the reflection haze pattern is substantially symmetric with the image center. In photo image 1200*b*, the reflection spot clusters 1202*b* and 1204*b* are aligned vertically to center with retinal image 1201*b* and the reflection haze pattern is substantially symmetric with the image center.

The symmetric haze pattern 1206*a* and symmetric reflection spot clusters 1203*a*, 1205*a*, 1202*b*, 1204*b*, along with the position of retinal details such as the optic nerve 1207*a* in the field of view, provide a visual judgment for the alignment of the wide field fundus camera 200B with the retina 2. Misalignment of the camera with respect to the central visual axis of the eye as measured by alignment errors in x, y, and z axis as well as tilt can be computed using the position of these reflection spot clusters 1203*a*, 1205*a*, 1202*b*, 1204*b* as well as the position of retinal details such as the optic nerve 1207*a* in the wide field retinal image 1200*a*, 1200*b*. With correct alignment of the wide field fundus camera 200B with the central axis of the eye the presence of standardized symmetric haze patterns 1200*a* and symmetric reflection spot clusters 1203*a*, 1205*a*, 1202*b*, 1204*b* enable efficient removal of the image haze using standardized digital masks.

The sequential photo images 1200*a* and 1200*b* are taken with electronic controller 50 of FIG. 2. The sequential photo images 1200*a* and 1200*b* are in one illustrative example preferably taken within a fraction of a second to avoid eye movement. In another preferred embodiment, sequential photo images are taken as four or more sectional images each sectional image with one pair of axially symmetric (e.g 1203*a*, 1205*a*) illumination beams generated by illumination beam projectors 230*n* to illuminate the retina. In a further preferred embodiment, sequential photo images are taken with illumination beam projectors 230*n* where said illumination beams are slit beams.

Figure 13A:
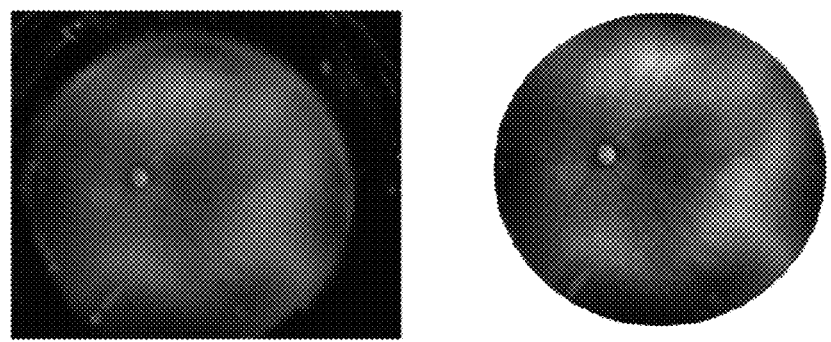
FIG. 13a shows an illustrative image of a single FOV montage generated with real-time dehazing and automated montage from the two images of FIG. 12a and FIG. 12b.
Figure 13B:
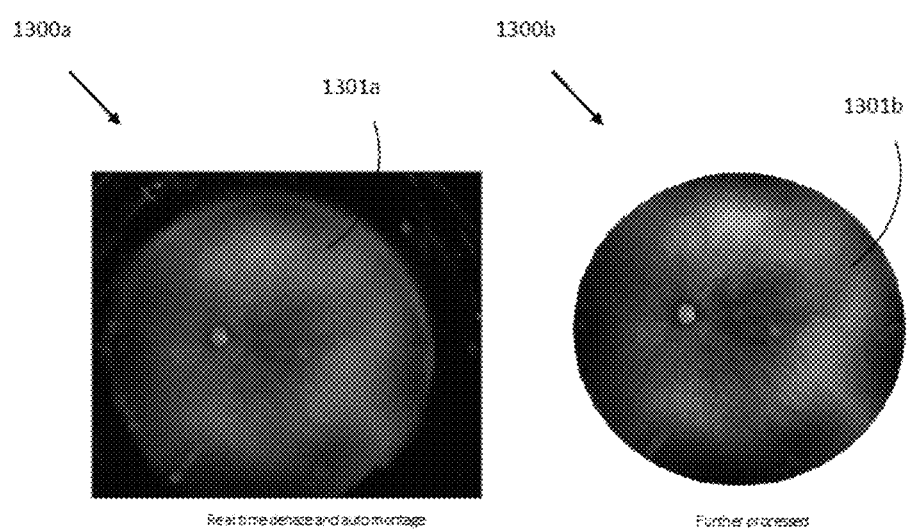
In FIG. 13b additional an additional dehaze algorithm has been performed on the single FOV to remove residual haze to further enhance visualization of ultra-wide FOV retinal detail.

FIG. 13*a* shows an illustrative automated montage image 1300*a* generated with real-time dehazing and auto-montage from the two sectional retinal images 1200*a* and 1200*b* of FIG. 12, and FIG. 13*b* shows a final montage image 1301*b* with further image enhancement as compared to the auto-montage image 1301*a*. As a result, a single montage 1301*b* is obtainable with a full ultra-wide FOV using the ultra-wide field lens (e.g. a combination of contact lens 12, inserted meniscus lens 12' and aspherical lens 10 of FIG. 3B) on the wide field camera 200B.

To obtain the automated montage image 1301*a*, real-time dehazing is performed on the sectional retinal images 1200*a* and 1200*b*, consisting of generation of an estimated haze map, digital masking of stereotypical haze and Purkinje reflection in said sectional retinal images, removal of additional haze from said masked sectional images by refining the transmission map using a reference haze free wide-field retinal image and dehazing of the masked sectional images using said transmission map. Dehazed masked sectional images are then montaged using the automated montage algorithm by aligning the sectional images using automatically generated control points, and then blending areas of overlap of said dehazed masked sectional images. This produces a seamless full FOV montage image 1300 *a* that has decreased haze and removal of Purkinje reflections as compared to the component sectional images 1200*a* and 1200*b*.

To obtain a final montage 1301*b*, a further dehazing is performed on the initial montage 1301*a* to remove residual haze and to enhance retinal image contrast. In a preferable embodiment, the instruction for a dehazing algorithm are computing processor-accessible and when executed further remove residual haze from the montage image 1301*a* and to create a haze-free montage image 1301*b*.

Instant auto-montage and haze-free image are highly desirable features of the ultra-wide field fundus camera 200B of FIG. 3B. It has been demonstrated that sequential photo images with horizontal spots 1200*a* and vertical spots 1200*b* can be taken within a fraction of a second to avoid eye movement and to simplify auto-montage process for instant auto-montage (e.g. in less 400 milliseconds). It has also been demonstrated that a dehazing algorithm can further remove residual haze from the montage 1301*a* and to create a haze-free full FOV montage image 1301*b* digitally and automatically.

Figure 14A:
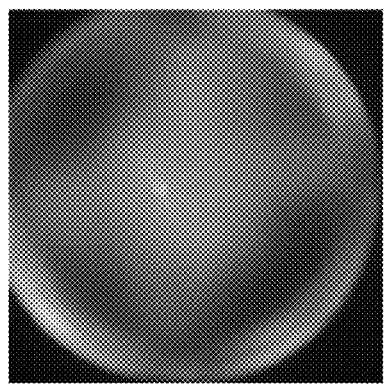
FIG. 14a shows an illustrative example of a retinal image needing to be spectrally dehazed.
Figure 14A:
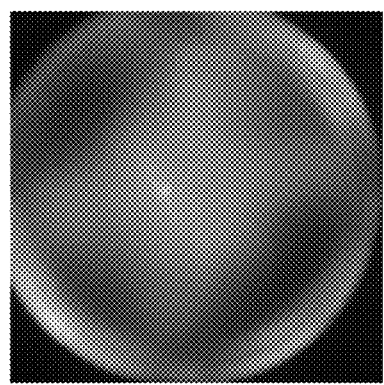
Figure 14B:
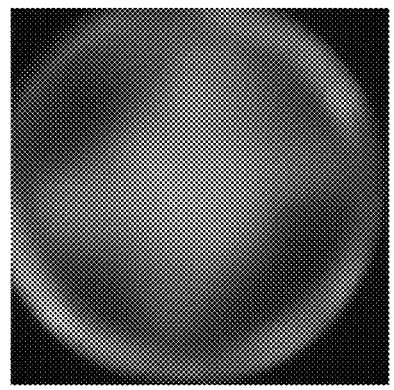
Figure 14C:
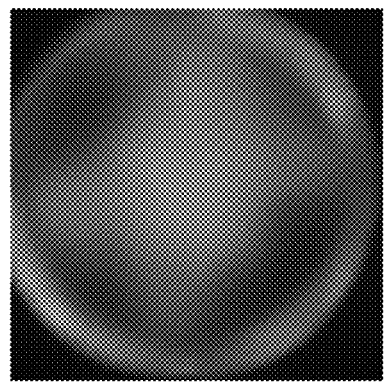
FIG. 14c shows an illustrative example of a Gaussian-blurred blue channel isolated from a retinal image for spectral haze mask creation. It was generated from FIG. 14b.
Figure 14D:
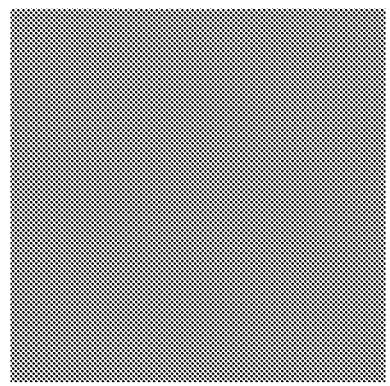
FIG. 14d shows an illustrative example of a bias image generated from the maximum intensity pixel of a blurred blue channel image. It was generated from FIG. 14c.
Figure 14E:
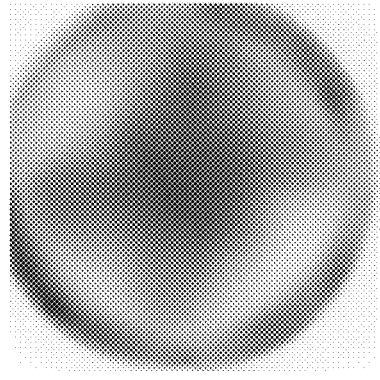
FIG. 14e shows an illustrative example of a transmission mask generated via blue channel spectral analysis of a retinal image. It was generated using FIG. 14c and FIG. 14d.
Figure 14F:
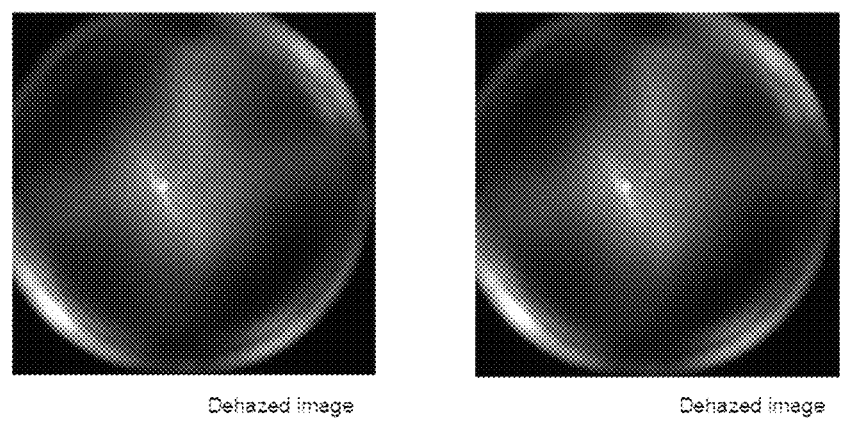
FIG. 14f shows an illustrative example of a retinal image dehazed via spectral analysis. It was generated from FIG. 14a, FIG. 14c, FIG. 14d, and FIG. 14e.

Such an ultra-wide FOV image of 1301*b* is thus taken at a single alignment position. Such a single alignment montage can thus be obtained via a standardized alignment procedure using said Purkinje reflections 1203*a* 1201*a* 1202*b* 1204*b* and visualization of said retinal structures such as the optic nerve 1107*a*, and a simplified auto-montage algorithm based on wide field fundus camera alignment with the central axis of the eye. As a result, such a single alignment 180-degree ultra-wide field montage can be taken within one sequential image acquisition so as to significantly reduce the number of image acquisitions needed to fully image the retina edge to edge FIG. 14*a* shows an illustrated example of a sectional retinal image prior to processing with the dehaze algorithm. In a preferred embodiment the image of 14*a* is processed according to a dehaze algorithm described in the flowchart for FIG. 17, generating an estimated haze map using the spectral characteristics of haze created by illumination beam projectors. In the example process of a preferred embodiment of the dehaze algorithm, the blue channel (FIG. 14a) is used as an estimated haze mask, which is made possible by spectral reflections from the retina primarily composed of red and green light. A blur process is used on the haze mask generated from the blue channel (FIG. 14c) to remove high frequency information that may contain retinal detail (so that the detail is not further masked out by the following steps in the dehaze algorithm). The brightest pixel in the blurred blue channel is selected and used to create a bias mask (FIG. 14d) by creating a greyscale RGB mask with all channel values equal to the brightest value in the blurred blue channel (FIG. 14c). Dividing the blurred blue channel by this bias normalizes the haze map. This map is then scaled down and inverted in order to produce a transmission mask (FIG. 14e) in which each pixel value is proportional to the signal-to-noise ratio of the corresponding pixel in the original input image. To apply this transmission mask to the source image, first the bias mask is subtracted from the input image, and then that difference is divided by the transmission mask. Finally, the bias mask is added back again to that quotient, any negative values in the resulting image are replaced with their absolute value, and then the image is clamped so that all no color is darker than pure black or brighter than pure white. The resultant dehazed image FIG. 14f improves the clarity of retinal details by removing reflected and scattered haze from the original wide field retinal image FIG. 14a.

The rationale behind the creation of the bias mask stems from an assumption that haze in the image is being produced by a diffuse ambient white light source. If the blue channel is taken to estimate the haze mask, then the brightest value in the blue channel can be taken as an estimate of the brightness of the ambient light source generating the haze. Furthermore, if a pixel position has a low transmission value (close to zero), then any channel value in the input image's corresponding pixel will become attenuated if its value is close to the bias value, and any channel value that is not close to the bias will be significantly scaled up (as a result of subtracting the bias and then dividing by the transmission value). This causes channel values that are likely the reflection of ambient light to be less emphasized, and channel values that are likely to carry information to be more emphasized.

Figure 15A:
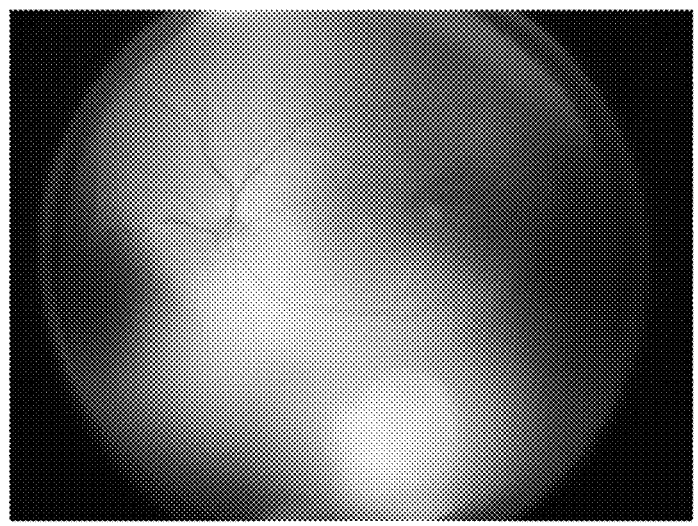
FIG. 15a shows an illustrative example of a retinal image demonstrating stereotypical illumination via a single beam illuminator.
Figure 15A:
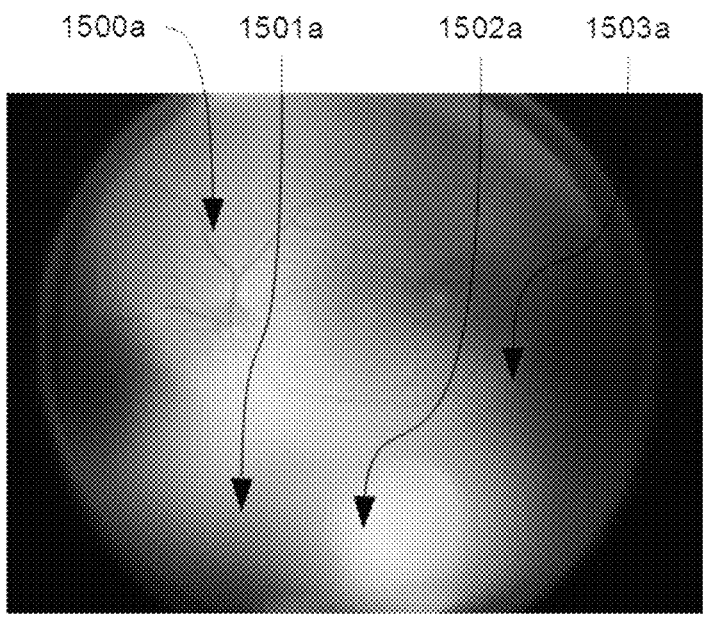
Figure 15B:
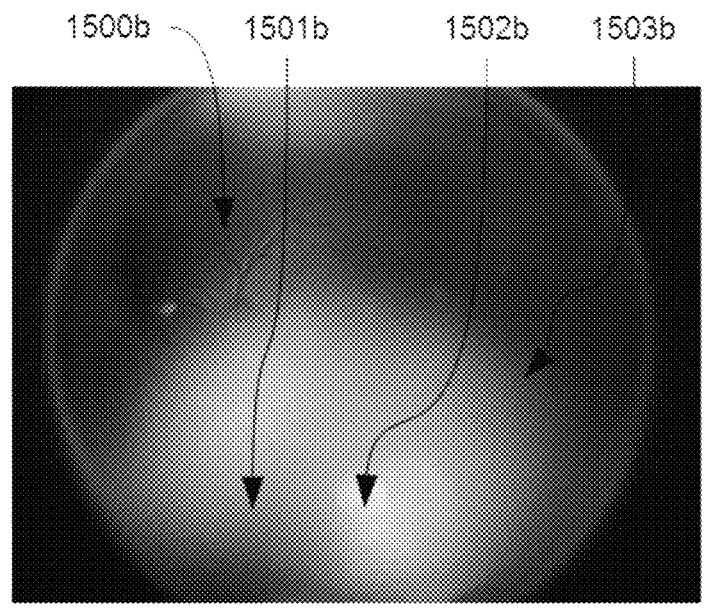
FIG. 15b shows an illustrative example of a stereotypical haze pattern produced via blue channel isolation of FIG. 15a. It can be used as a model for the expected haze pattern resulting from imaging a retina under the same camera alignment and illumination conditions.

FIG. 15a shows an illustrative example of a sectional retinal image demonstrating stereotypical illumination resulting from a single beam illuminator with the camera at a near-central alignment. 1500a marks a well-exposed region of the retina, 1501a marks a spot shrouded in diffuse haze, 1502a is in the midst of a P1 Purkinje reflection, and 1503a is located on the border separating a well-exposed portion of the retina from the region shrouded in diffuse haze. Knowledge of which illumination beam projectors are illuminated allows the resulting haze pattern on the retina to be estimated by simple reference to the stereotypical haze pattern shown in FIG. 15a for the given wide-field lens and given wide-field FOV. This pattern can additionally in another illustrative example be characterized by the blue channel component of the sectional retinal image as shown in FIG. 15b.

Figure 15C:
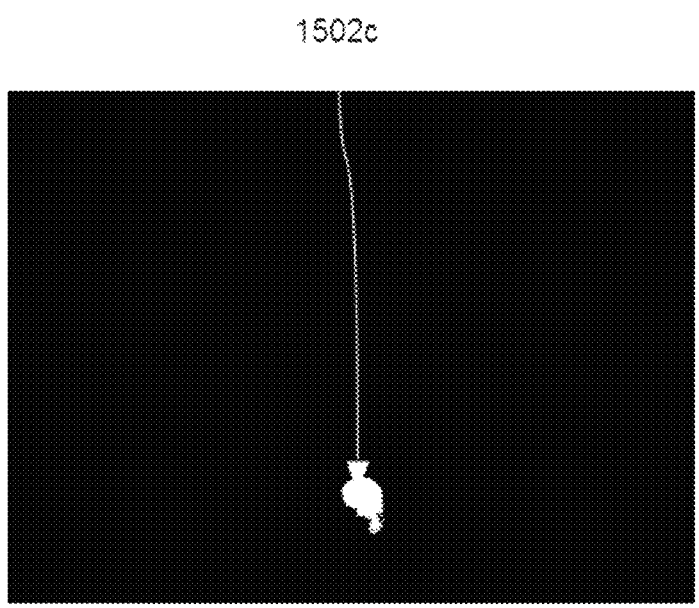
FIG. 15c shows an illustrative example of the result of an image thresholding operation used to detect Purkinje reflections. It was generated from FIG. 15b.

FIG. 15c demonstrates an illustrative example using image thresholding of the image in FIG. 15a to automatically identify the Purkinje P1 reflection 1502c. In an alternate embodiment, the Purkinje reflection can be identified by shape and by spectral frequency in the wide-field FOV image. Purkinje reflections will move within the wide field FOV dependent on camera alignment with the central visual axis. Automated detection of the purkinje reflection allows calculation the centration of alignment of the wide-field fundus camera with the eye. Knowledge of wide field fundus camera alignment with the eye can inform dehaze and auto montage algorithms to enhance removal of reflected and scattering haze from wide-field retinal images and perform automated montage of sectional images having improved clarity of retinal details.

Figure 16A:
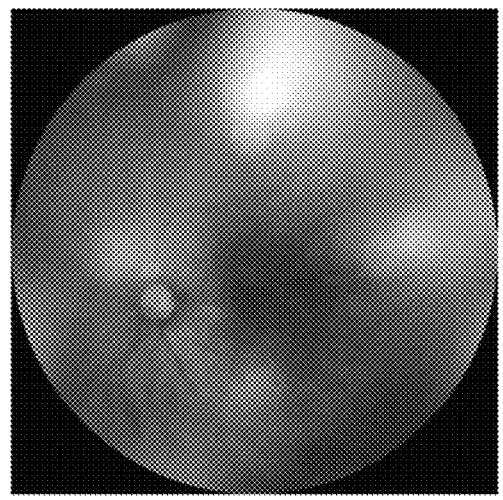
FIG. 16a shows an illustrative example of a retinal image taken with optimal camera alignment and symmetric illumination via 4 beam illuminators.
Figure 16A:
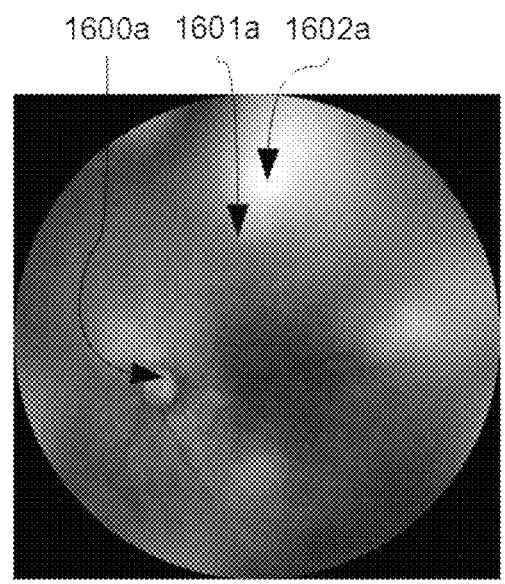

FIG. 16a shows an illustrative example of a wide-field FOV retinal image taken at central alignment with 4 beam illuminators. 1600a marks the optic nerve, 1601a marks the topmost purkinje P1 reflection, and 1602a marks the topmost purkinje P4 reflection.

Figure 16B:
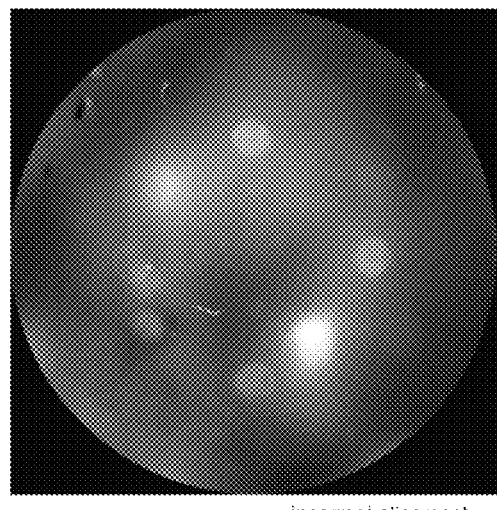
Figure 16B:
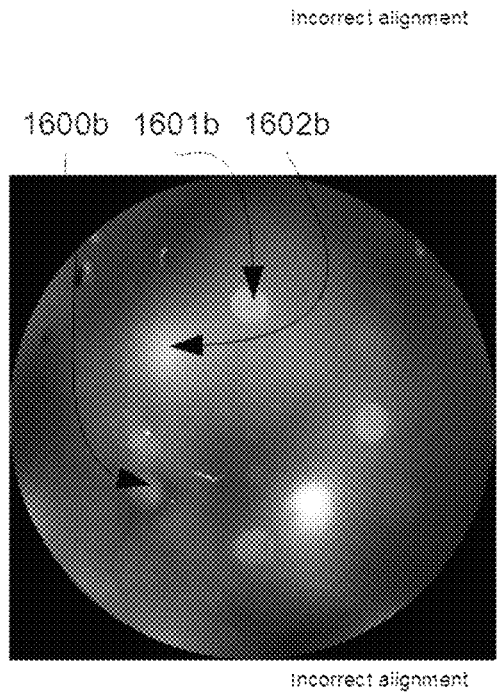

FIG. 16b shows an illustrative example of a wide-field FOV retinal image taken at a skewed alignment with 4 beam illuminators. It shows the same retina seen in FIG. 16a. The nerve at 1600b has much less detail due to the misalignment, although its position within the wide-field FOV does not appear to have changed much to the naked eye relative to 1600a. The obvious change is seen at 1602b where the topmost purkinje P4 reflection 1602b has moved a large distance away from the topmost purkinje P1 reflection 1601b. The purkinje P4 reflection 1602b has high contrast with the retina and is easily detected automatically, as shown in FIG. 16c at 1602c.

Figure 16C:
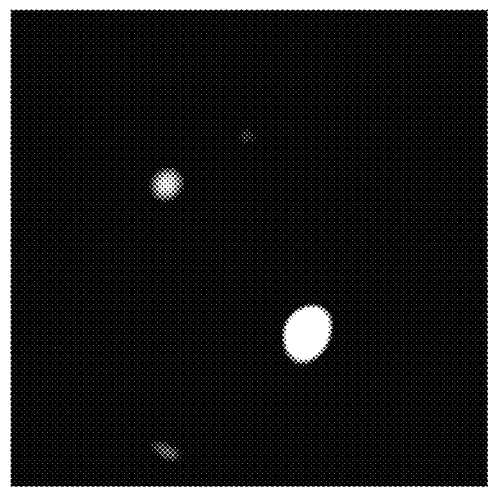
FIG. 16c shows an illustrative example of P4 reflections detected and isolated from P1 reflections via difference of Gaussians and thresholding.

FIG. 16c shows an illustrative example of automated purkinje P4 detection at 1602c. In this illustrative example thresholding is used to eliminate all but the Purkinje reflections, and difference of Gaussians is used to further differentiate the purkinje P4 reflection 1602b form the purkinje P1 reflections 1601b. A vector can be computed that originates at 1601b and extends to 1602c because the P1 reflection at 1601b is static and can be stereotyped for various optical configurations. Such a vector can be used to compute a magnitude and direction of camera tilt misalignment with the retina. If more than one such vector as used by detecting more than one pair of purkinje P1 and P4 reflections, then it is possible to compute the rotation angle of misalignment.

Computing camera alignment makes it feasible to stereotype and model reflection and haze patterns at various alignments, as opposed to only for a central view shown in FIG. 15. This creates the opportunity to augment the spectral dehazing process described in FIG. 14. The blue channel haze mask can be refined by an estimated haze mask produced by an optical model that operates by considering the illuminator pattern and the automatically-detected camera alignment.

Figure 17:
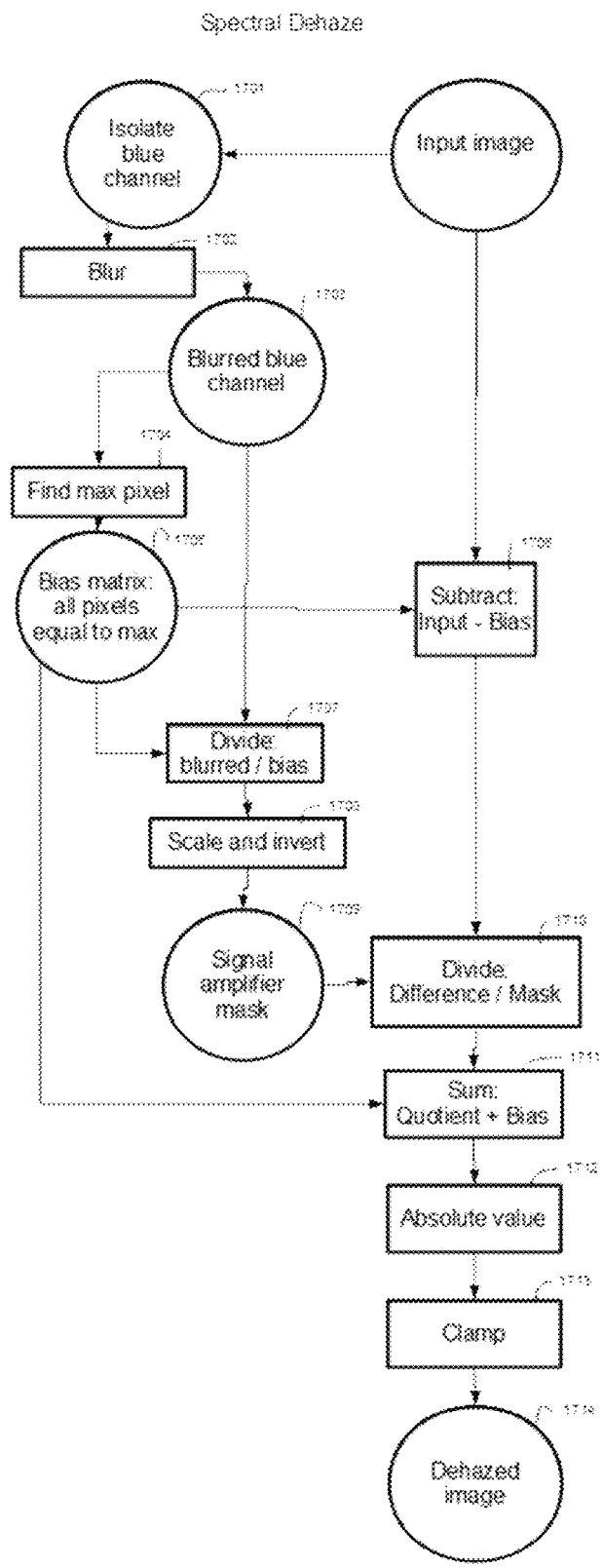
FIG. 17 shows a flow chart of an example procedure for dehazing a retinal image via spectral analysis.

FIG. 17 shows an illustrative example of a spectral dehaze algorithm. It works as described in earlier descriptions of FIG. 14.

Figure 18:
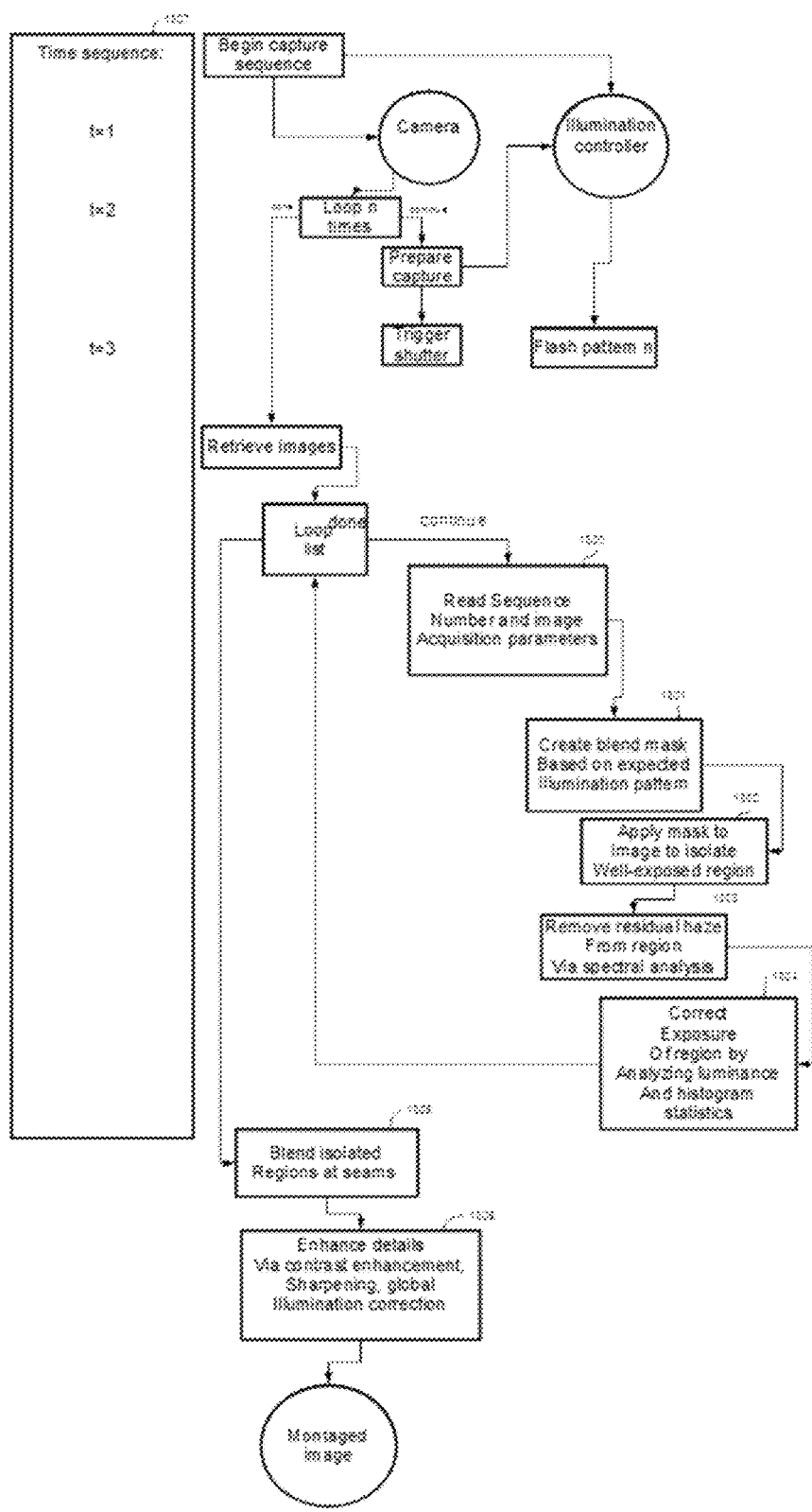
FIG. 18 shows a flow chart of an example procedure for performing automatic montage image montage.

FIG. 18 shows an illustrative example of an algorithm that seamlessly montages a set of sequential retinal images taken in a central alignment. The flow chart represents multiple sequences of events happening in parallel by the time bar at 1807. All event boxes in the chart that are located on the same horizontal line (and thus the same t value) occur simultaneously. This is only critical for the image capture sequence preceding the montage algorithm that spans t values of 1, 2, and 3.

The sequential sectional images in this process are taken at high-speed with a set pattern of flashing illumination beam projectors. The camera encodes the sequential order of each image inside the image acquisition parameters located in the image file data. Step 1800 reads this data from each image to determine the image's sequence number, which is used to generate a static blending mask (1801) that is stereotyped based on the expected illumination beam projector flash pattern. At 1802, this mask is used to isolate the well-exposed region of each image. Each image is spectrally dehazed in 1803, and in 1804 is illumination-corrected via histogram and luminance analysis. 1804 ensures that each region will have the same final light exposure before being blending together, so that the four source regions can be easily identified in the final image. Finally at 1805, each image is blended at the seams. Final image enhancement occurs at 1806, taking advantage of global statistics available by having the entire FOV in a single image. This produces the final statically-montaged image.

Figure 19:
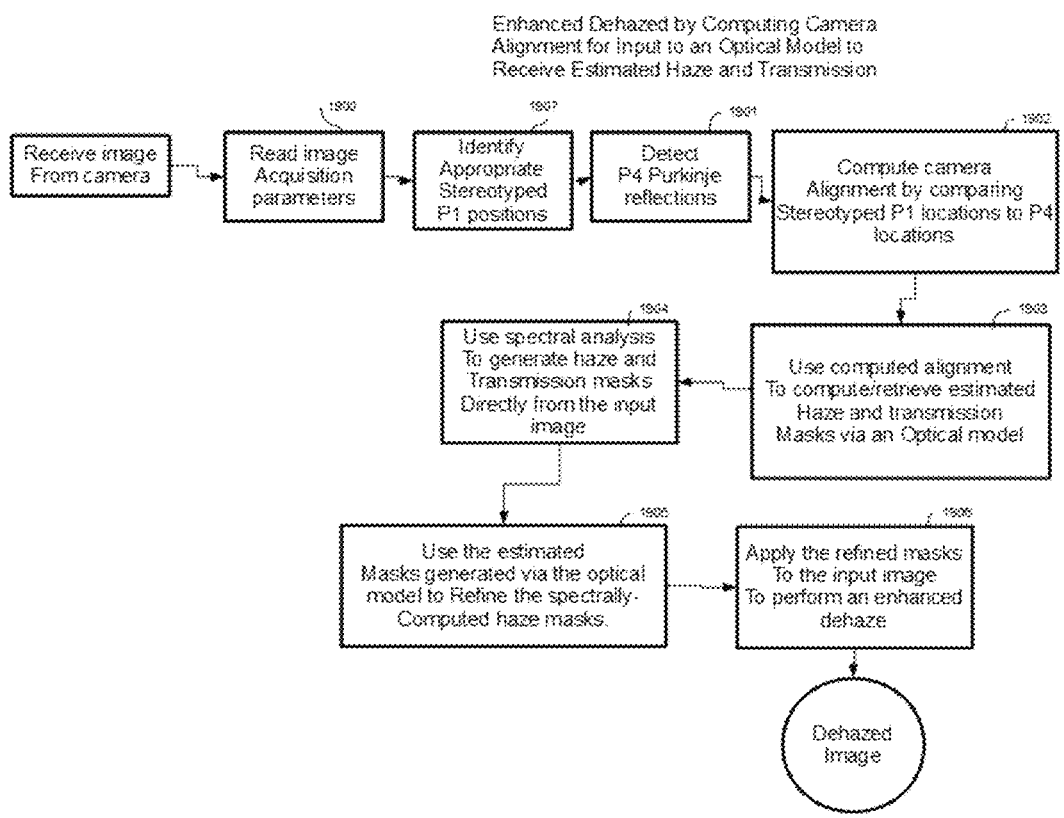
FIG. 19 shows a flow chart of an example procedure for enhancing retinal image spectral dehazing by using camera alignment information computed following Purkinje reflection position detection in order to compute/retrieve estimated haze and transmission masks via a reference optical light scattering model.

FIG. 19 shows an illustrative example of an algorithm that uses an optical model and computed camera alignment information to produce estimated haze and transmission masks that are used to refine a separate set of haze and transmission masks generated by a spectral dehaze algorithm such as the one exemplified in FIG. 14 and FIG. 17. At 1900, the algorithm receives the camera image from which it reads the image acquisition parameters to know the illumination beam projector pattern that was flashed at acquisition time. This is used to select a stereotyped set of expected purkinje P1 locations. Purkinje P4 reflections are identified at 1901 by an algorithm such as the one demonstrated in 1602c. Then their positions are compared to the stereotyped purkinje P1 positions in order to derive camera position information, such as by a process described in the details of FIG. 16. With alignment information and illuminator information known, a first set of estimated haze and transmission masks are calculated at 1903 using the optical model, and then at 1904 spectral analysis on the input image is used to generate a second set of haze and transmission masks. There are many possible embodiments to implement 1905 to obtain alternate refined haze masks. One possible embodiment is to compute the pointwise minimum of the two sets of masks. This will underestimate the amount of haze present, resulting in a more moderate effect on the final image but with the lowest chance of losing retinal image detail. An alternate embodiment is to average the masks, so that the resulting haze mask matches both input masks at pixels where they agree, and produces a middle-ground estimate for pixels where they disagree. At 1906, the masks are applied to the image to produce the final dehazed image output.

Figure 20:
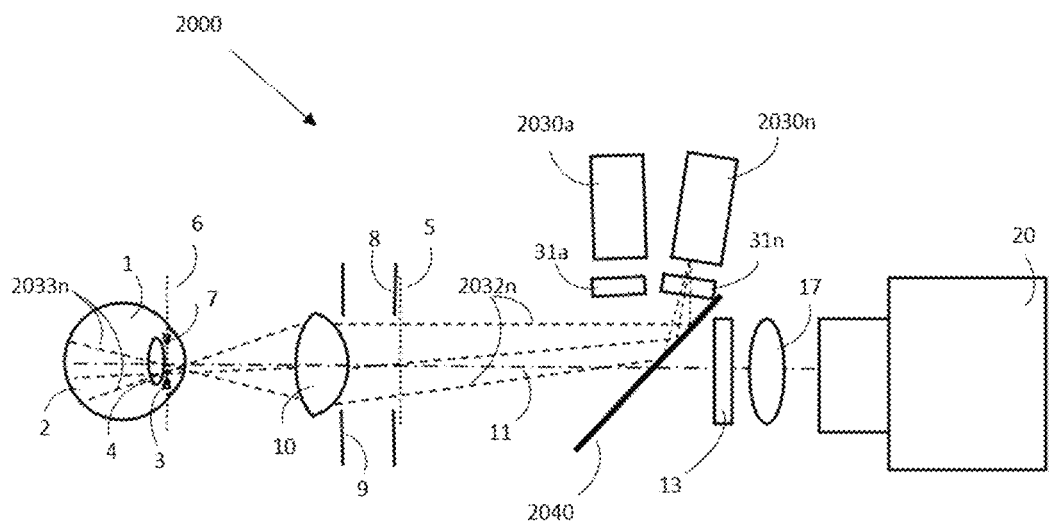
FIG. 20 shows an illustrative example of wide field fundus camera having the illumination beam projectors optically coupled to the central viewing axis using a beam splitter or mirror.

FIG. 20 shows an illustrative example of a wide field fundus camera 2000 having an illumination beam projector 2030n turned on for taking one of the multiple sectional retinal images. The illumination beam projector 2030n and 2030a in a preferred embodiment are optically coupled to the central viewing axis 11 using a beam-splitter or mirror 2040. The illumination beam projector 2030n and 2030a in an alternate embodiment may be optically coupled to a plurality of mirrors or beamsplitters to direct light from the projectors along the central viewing axis 11. The illumination beam 2032n projected from the illumination beam projector 2030n is focused on the working plane 6. The illumination beam 2032n then passes through the subject pupil 3 and turns into illumination beam 2033n to illuminate the subject retina 2.

The illumination beam 2032 can be projected at an angle with respect to the central viewing axis 11. In an illustrated example, the illumination beam path does not overlap with the image beam path throughout the crystalline lens 4. In this way, image recording device 20 does not capture the light scattered from the crystalline lens 4. Consequently, the image noise from the scattering light may be significantly reduced.

Figure 21A:
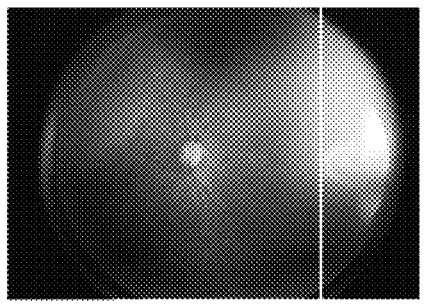
FIG. 21a-21g show the formation of an illustrative example of a montage where the wide field fundus camera is in a non-central alignment with respect to the eye.
Figure 21B:
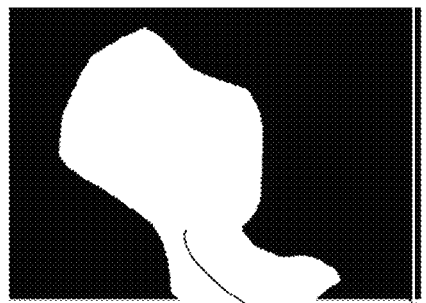
Figure 21C:
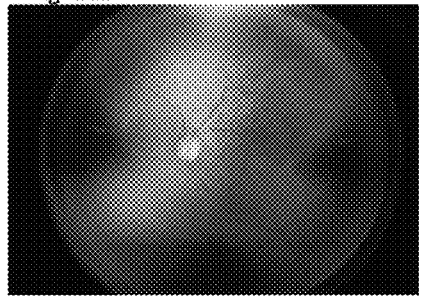
Figure 21D:
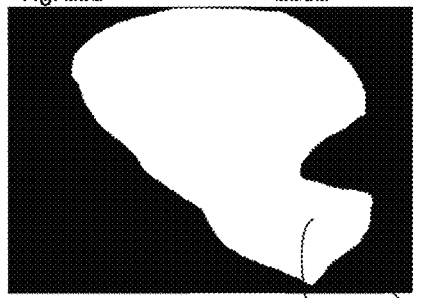
Figure 21E:
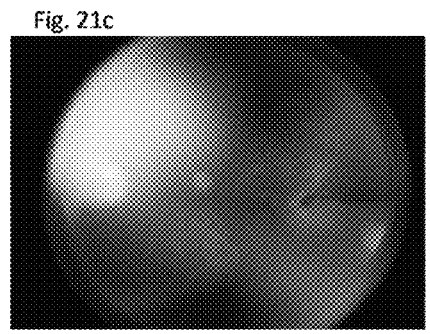
Figure 21F:
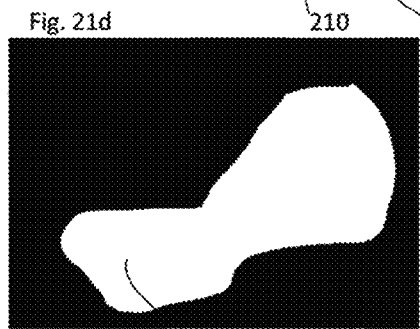
Figure 21G:
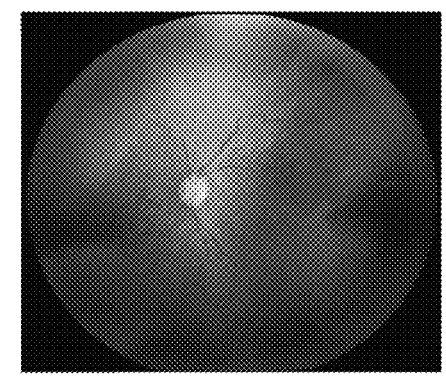
Figure 22A:
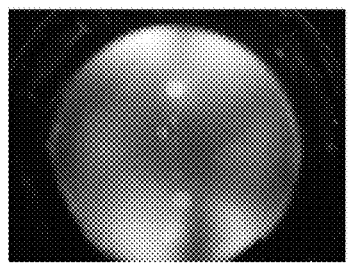
FIG. 22a-22e show the formation of an illustrative example of a montage with assumed symmetry of retinal illumination and haze due to central alignment of the wide field camera with the central axis of the eye.
Figure 22B:
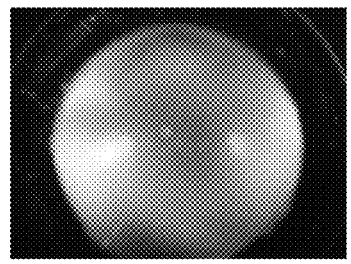
Figure 22C:
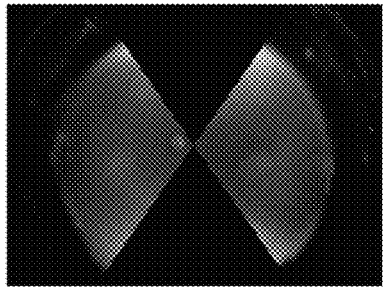
Figure 22D:
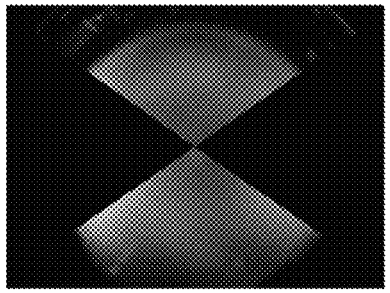
Figure 22E:
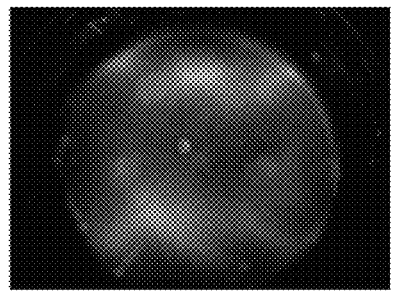

FIGS. 21a-21g show the formation of an example of a montage where the wide field fundus camera is in a non-central alignment with respect to the eye. Using computed alignment of the wide field fundus camera with respect to the eye, asymmetries in the reflected and scattered haze as well as retinal illumination can be adjusted for. FIGS. 21b, 21d and 21f illustrate how the dynamic mask might manifest for retinal images shown in FIGS. 21a, 21c and 21e respectively. The black areas 2101, 2103 and 2105 would be regions to exclude whereas white regions 2102, 2104 and 2106 would be the regions to include in the montage. As a result, a single montage FIG. 21g can be obtained with a full FOV defined with the ultra-wide field lens while substantially reducing the noise of the image.

FIGS. 22a-22e show the formation of an example of a montage with assumed symmetry of retinal illumination and haze due to central alignment of the wide field camera with the central axis of the eye. Consequently, a static mask may be used to exclude the symmetrical retinal haze in favor of the sectional images shown in FIGS. 22a and 22b. When montaged, the results may resemble the final image FIG. 22e with a full FOV defined with the ultra-wide field lens.

Figure 23:
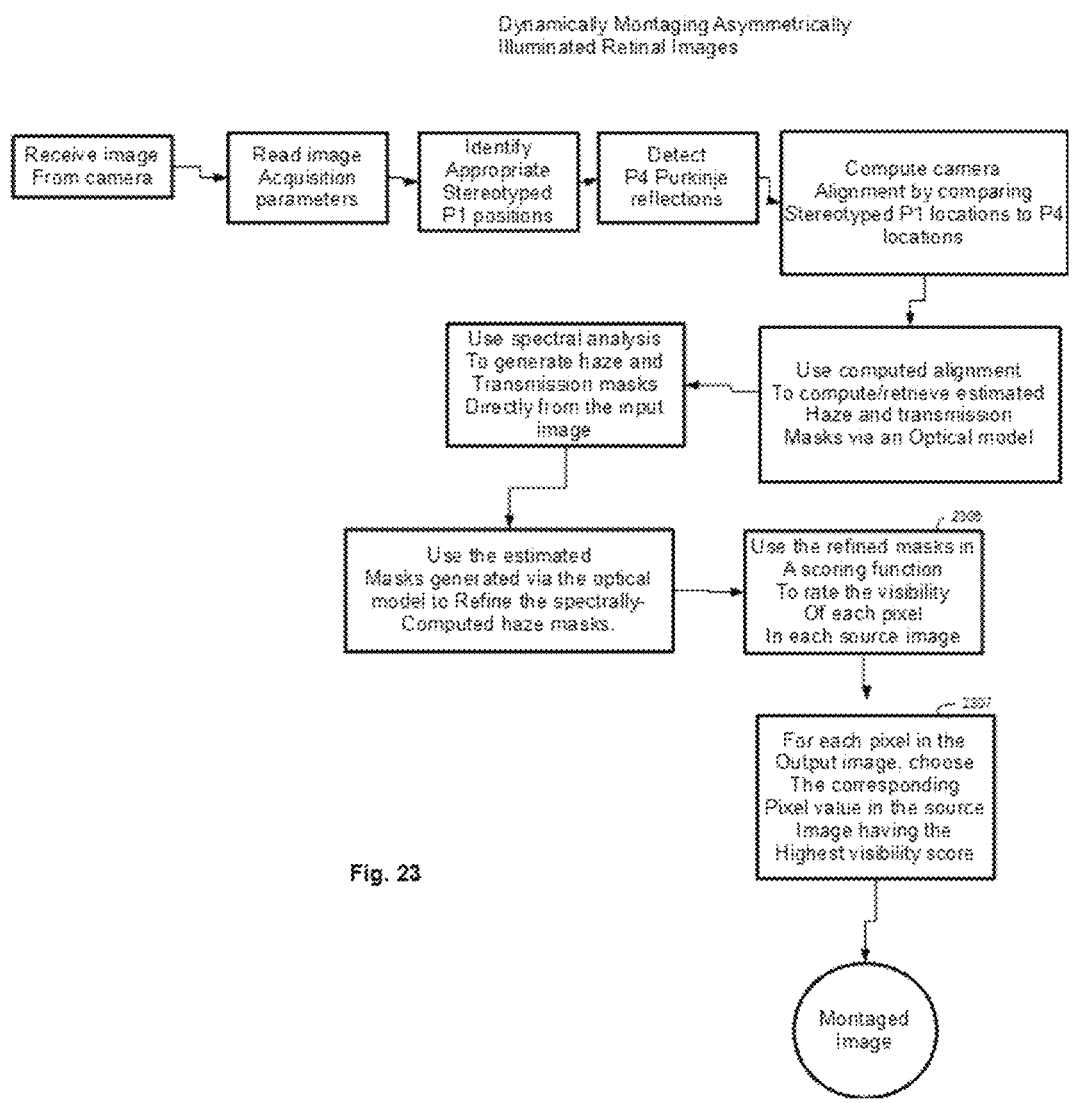
FIG. 23 shows an illustrative example of an algorithm that can be used to dynamically generate montaging masks for asymmetrically illuminated retinal images.

FIG. 23 shows an illustrative example of an algorithm that can be used to generate dynamic montaging masks for montaging asymmetrically illuminated retinal images. It contains all of the steps of the enhanced dehaze algorithm described in FIG. 19 because the refined haze and transmission maps that are generated from that process are useful for deciding where to source pixel values at various pixel locations in the output image. The dynamic montage algorithm applies the enhanced dehaze processing steps in order to generate haze masks for each input image. Those masks are then used to score the visibility of each pixel in each source image. Finally, each pixel in the output image obtains its value from the corresponding pixel in one of the source images by choosing the corresponding pixel having the highest visibility score among all of the source images.

The above-detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As defined herein a "computer readable storage medium" is defined as a tangible device that can retain and store instructions for use by an instruction execution device. The computer readable storage medium may be, for example, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A wide field fundus camera, comprising:
    an objective lens having a viewing axis and disposed to form a retinal image, the objective lens being a wide field aspherical lens having a FOV of at least 60 degrees;
    an image recording device disposed to capture said retinal image of a wide field of view;
    a plurality of illumination beam projectors positioned around said viewing axis and each configured to project an illumination beam at an angle toward said objective lens;
    a mechanism of cross polarization configured between said image recording device and said plurality of illumination beam projectors to reject specular reflections of said illumination beams;
    an image display operatively coupled to the image recording device to display said retinal image from said image recording device;
    an electronic controller operatively coupled to said plurality of illumination beam projectors to provide power to each of the plurality of illumination beam projectors in a predetermined sequence to provide illumination to obtain each of a plurality of retinal images;
    a dehazing algorithm implemented to remove reflections and scattered light haze from said plurality of retinal images; and
    an automated montage algorithm implemented to produce a montage of said plurality of retinal images into a single image of said wide field of view.

2. The wide field fundus camera of claim 1, further comprising:
    a second dehazing algorithm implemented to further remove reflected and scattered light haze from said montage.

3. The wide field fundus camera of claim 1, wherein said objective lens is a wide field aspherical lens having a FOV of 60 degrees to 160 degrees.

4. The wide field fundus camera of claim 1, wherein said objective lens is an ultra-wide field objective lens having a FOV of 160 degrees or wider.

5. The wide field fundus camera of claim 1, wherein said objective lens is an ultra-wide field objective lens system comprising a contact lens, a meniscus lens and an aspherical lens.

6. The wide field fundus camera of claim 1, wherein said dehazing algorithm identifies reflected and scattered light haze in said retinal images by the position of said haze.

7. The wide field fundus camera of claim 1, wherein said dehazing algorithm identifies reflected and scattered light haze in said plurality of retinal images by spectral content of said haze.

8. The wide field fundus camera of claim 1, wherein said plurality of illumination beam projectors comprises of 8 projectors positioned to provide eight reflection spot clusters at 12, 1:30, 3, 4:30, 6, 7:30, 9, and 10:30 o'clock positions on an eye positioned along the viewing axis.

9. The wide field fundus camera of claim 8, wherein 4 of the 8 projectors form a first subset providing infrared illumination, and another 4 of the 8 projectors form a second subset providing white light illumination, each of the first subset and the second subset being symmetrically disposed around the viewing axis.

10. The wide field fundus camera of claim 1, wherein said dehazing algorithm comprises processor-accessible instructions for dehazing an image, that when executed perform acts comprising the steps of:
    computing positions of Purkinje reflections from said wide field fundus camera produced by said illumination beam projectors;
    computing wide field fundus camera alignment with a central axis of an eye being imaged by said wide field fundus camera using the positions of said Purkinje reflections within said single image;

computing an estimated haze map for said wide field fundus single image using a reference ocular corneal and lens reflected and scattering haze model for said illumination beam projectors at said camera alignment with said central axis;

computing a digital mask for removal of reflected and scattering haze from said single image using an estimated haze map;

computing a processed masked wide field image from said single image by removal of portions of said single image covered by said digital mask;

computing a transmission map utilizing the estimated haze map for said single image;

refining the transmission map for said single image using a reference retinal wide field fundus image; and reconstructing a retinal image from said masked image using the refined transmission map to dehaze the masked image and to produce a dehazed masked wide field retinal image.

11. The wide field fundus camera of claim 1, wherein said dehazing algorithm comprises processor-accessible instructions for dehazing an image, that when executed perform acts comprising the steps of:

computing an estimated haze map using at least one of a reference spectrum and size and spatial distribution of said reflections and scattered light haze;

computing a transmission map utilizing estimated haze map for said single image;

refining the transmission map utilizing estimated retinal transmission from a reference retinal wide field fundus image; and using the refined transmission map to dehaze the single image to produce a dehazed wide field retinal image.

12. The wide field fundus camera of claim 1, wherein said automated montage algorithm comprises processor-accessible instructions that, when executed, perform acts comprising the steps of:

computing position of Purkinje reflections produced by said illumination beam projectors;

computing wide field fundus camera alignment with a central axis of an eye being imaged by said wide field fundus camera using the position of said Purkinje reflections within said plurality of images;

computing an area of each the plurality of images to be included in said single montage image and creating a sectional image digital mask for each of the plurality of images to remove scattering haze and the Purkinje reflections, determined by said wide field fundus camera alignment;

computing a masked sectional image from each of said plurality of images by removal of an area of each of the plurality of images covered by each said sectional image digital mask;

computing a blending of overlapping areas of each masked sectional image using at least one of camera alignment, image haze, image focus, image spatial frequencies, and image sharpness to preserve image detail and removing discontinuities between the plurality of images in the single image to create a seamless montage; and computing an image projection for said montage image using said wide field fundus camera alignment to minimize montage image distortion.

13. The wide field fundus camera of claim 1, wherein said automated montage algorithm comprises processor-accessible instructions, that when executed perform acts comprising the steps of:

computing positions of Purkinje reflections produced by said illumination beam projectors;

computing wide field fundus camera alignment with a central axis of an eye being imaged by said wide field fundus camera using the position of said Purkinje reflections within said plurality of images;

computing an estimated haze and transmission map for said single image using a reference ocular corneal and lens reflected and scattering haze model for said illumination beam projector at said camera alignment with a central axis of a reference model eye;

computing a haze and transmission map directly from the single image using spectral analysis of illumination by the plurality of illumination beam projectors in the single image;

refining the transmission map generated by spectral analysis of said single image utilizing the estimated map;

computing a scoring function to rate visibility of each pixel in each of the plurality of images using the refined transmission map; and selecting, for each pixel in the single image, corresponding pixel value in the plurality of images having a highest visibility score.

* * * * *